United States Patent [19]

Greve et al.

[11] Patent Number: 4,591,635
[45] Date of Patent: May 27, 1986

[54] SULFO GROUP-FREE POLYAZO COMPOUNDS CONTAINING AT LEAST TWO BASIC WATER-SOLUBILIZING GROUPS IN METAL-FREE OR METAL COMPLEX FORM

[75] Inventors: Manfred Greve, Dornach; Helmut Moser, Oberwil, both of Switzerland

[73] Assignee: Sandoz Ltd., Basel, Switzerland

[21] Appl. No.: 550,862

[22] Filed: Nov. 10, 1983

[30] Foreign Application Priority Data

Nov. 22, 1982 [DE] Fed. Rep. of Germany ....... 3243092
Feb. 7, 1983 [DE] Fed. Rep. of Germany ....... 3304031

[51] Int. Cl.$^4$ .................. C09B 35/039; C09B 44/02; C09B 44/08; D06P 1/41
[52] U.S. Cl. .................. 534/612; 534/604; 534/605; 534/606; 534/608; 534/615; 534/738; 534/755; 534/708
[58] Field of Search .......... 534/606, 608, 604, 605, 534/612, 708, 738, 755, 615

[56] References Cited

U.S. PATENT DOCUMENTS 3,691,148  9/1972  Peter et al. .................. 534/608
4,065,254  12/1977  Buhler et al. .................. 8/1

FOREIGN PATENT DOCUMENTS 56574  7/1982  European Pat. Off. ........... 534/606
62824  10/1982  European Pat. Off. ........... 534/606
62825  10/1982  European Pat. Off. ........... 524/606
1547900  6/1979  United Kingdom .............. 524/606
1550830  8/1979  United Kingdom .............. 524/608
2121814  1/1984  United Kingdom .............. 534/608

Primary Examiner—Floyd D. Higel
Attorney, Agent, or Firm—Gerald D. Sharkin; Richard E. Vila; Melvyn M. Kassenoff

[57] ABSTRACT

Metal-free compounds and 1:1 and 1:2 metal complexes of the formula

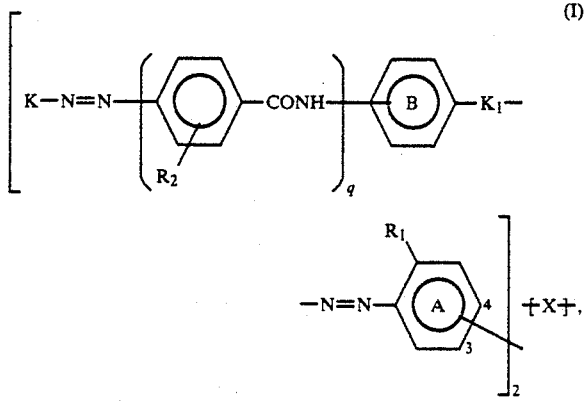

or a 1:2 metal complex of a metal-free compound of said formula and a metallizable azo compound not of said formula, wherein each K is independently a coupling component radical of the pyrazolone-5, 5-aminopyrazole, pyridone, 2,6-diaminopyridine, β-naphthol, acetic acid ester, acetic acid amide or N-substituted N,N-disubstituted aniline series, each $K_1$ is independently

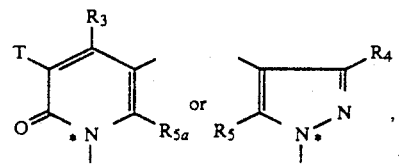

wherein
$R_3$ is hydrogen, $C_{1-4}$alkyl, phenyl or benzyl,
$R_4$ is $C_{1-4}$alkyl, ($C_{1-4}$alkoxy)-carbonyl or —CO—N($R_8$)$_2$, wherein each $R_8$ is independently hydrogen or $C_{1-4}$alkyl,
$R_5$ is amino or hydroxy,
$R_{5a}$ is hydroxy,
T is hydrogen, cyano,

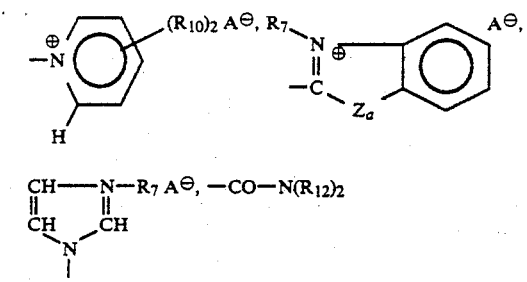

or ($C_{1-4}$alkyl)carbonyl, wherein $R_7$, $R_{10}$, $R_{12}$, $Z_a$ and $A^\ominus$ are as defined in the specification, each $R_1$ is independently hydrogen, halo, hydroxy, $C_{1-4}$alkoxy or $C_{1-4}$alkyl, or $R_1$ and $R_5$, located on rings attached to the same azo radical, are —O—Me—NH or —O—Me—O—, wherein Me is a 1:1 or 1:2 metal complex-forming metal ion, or $R_1$ and $R_{5a}$, located on rings attached to the same azo radical, are —O—Me—O—, wherein Me is as defined above, each $R_2$ is independently hydrogen, halo, $C_{1-4}$alkyl or $C_{1-4}$alkoxy, X is a direct bond or a bridging radical as defined in the specification, and each q is independently 0 or 1, with the provisos that (i) the compound of Formula I has at least two basic water-solubilizing groups, and (ii) each end of X is in a 3- or 4-position of the Ring A to which it is attached, which metal-free compounds and 1:1 and 1:2 metal complexes are useful as dyes, particularly for paper and leather.

15 Claims, No Drawings

SULFO GROUP-FREE POLYAZO COMPOUNDS CONTAINING AT LEAST TWO BASIC WATER-SOLUBILIZING GROUPS IN METAL-FREE OR METAL COMPLEX FORM

The invention relates to sulpho group-free azo compounds in metal-free or metallised form, which are useful as dyestuffs.

According to the invention there is provided compounds which in metal-free form are of formula I

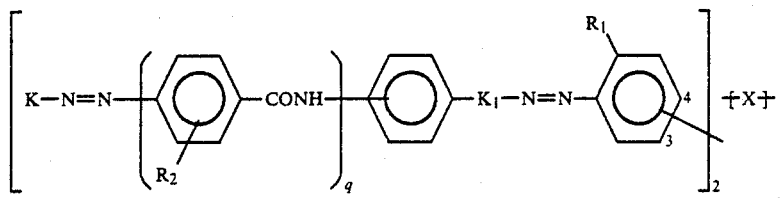

in which each K independently is the residue of a coupling component of the pyrazolone-5 series, the 5-aminopyrazole series, the pyridone series, the β-naphthol series, the 2,6-diaminopyridine series, the acetic acid ester series or acetic acid amide series or N-substituted or N,N-disubstituted aniline series;

each $R_1$ independently is selected from hydrogen, halogen, hydroxy, unsubstituted $C_{1-4}$alkoxy and unsubstituted $C_{1-4}$alkyl, each $R_2$ independently is selected from hydrogen, halogen, unsubstituted $C_{1-4}$alkyl and unsubstituted $C_{1-4}$alkoxy;

each q independently is 0 or 1;

each $K_1$ independently is selected from a group of formula II or formula III

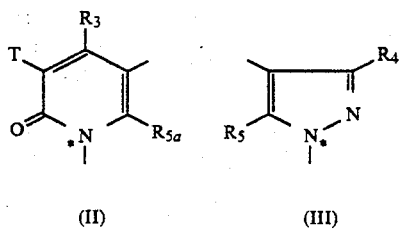

in which the starred atom is attached to the phenyl group;

each $R_3$ independently is selected from hydrogen, unsubstituted $C_{1-4}$alkyl, unsubstituted phenyl and unsubstituted benzyl;

each $R_4$ independently is selected from unsubstituted $C_{1-4}$alkyl and —CO—$R_6$;

each $R_5$ independently is —$NH_2$ or —OH and each $R_{5a}$ is —OH;

each $R_6$ independently is $C_{1-4}$alkoxy or —N($R_8$)$_2$;

each $R_8$ independently is hydrogen or unsubstituted $C_{1-4}$alkyl;

each T independently is hydrogen, —CN,

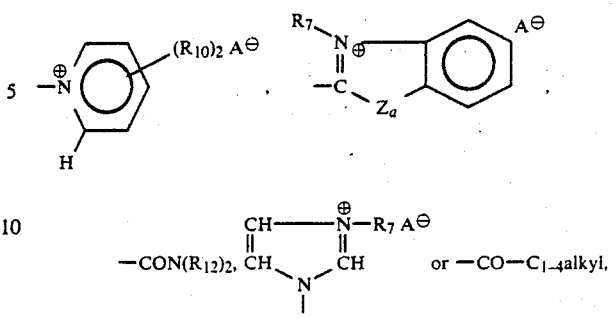

where $R_7$ is unsubstituted $C_{1-4}$alkyl;

each $R_{10}$ independently is hydrogen, —N($R_{12}$)$_2$, —CON($R_{12}$)$_2$ or unsubstituted $C_{1-4}$alkyl;

each $Z_a$ independently is —S—, —O— or $$-N-R_8;$$

each $R_{12}$ independently is hydrogen, unsubstituted cyclohexyl or $C_{1-4}$alkyl unsubstituted or substituted by one —OH group;

$A^{\ominus}$ is a non-chromophoric anion;

X, when both $R_1$'s are hydrogen, is $X_1$ to $X_{73}$;

$X_1$ a direct bond, $X_2$ a linear or branched unsubstituted $C_{1-4}$alkylene group, $$X_3 -CO-, X_4 -NH-\overset{S}{\overset{\|}{C}}-NH-, X_5 -S-, X_6 -O-,$$

$$X_7 -CH=CH-, X_8 -S-S-, X_9 -SO_2-,$$

$$X_{10} -NH-, X_{11} -NH-CO-, X_{12} -\underset{CH_3}{\overset{|}{N}}-CO-,$$

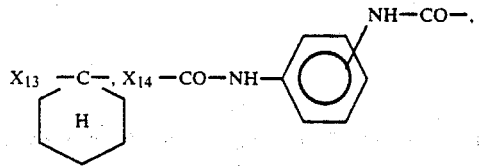

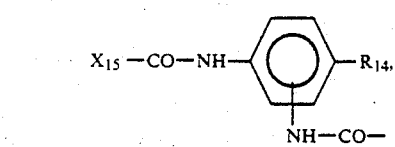

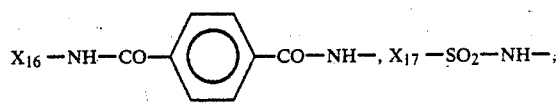
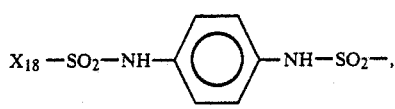
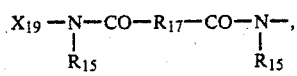
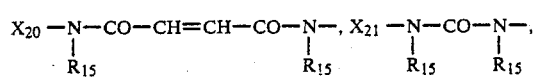
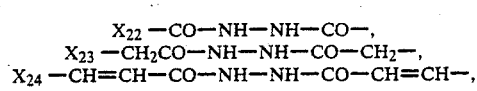
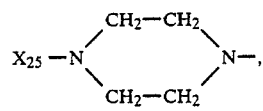
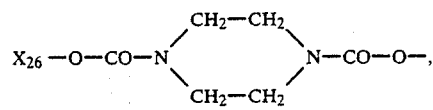
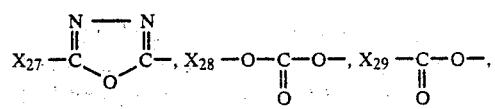
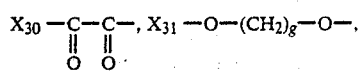
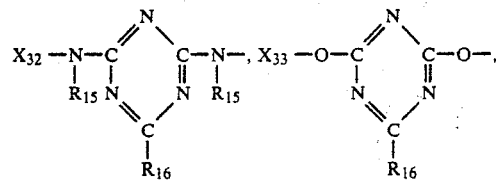
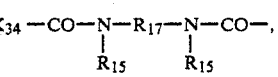
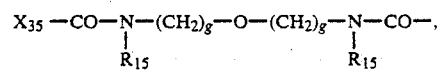
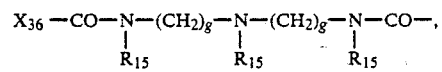
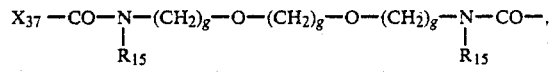
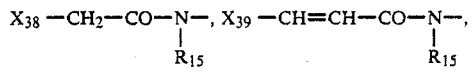
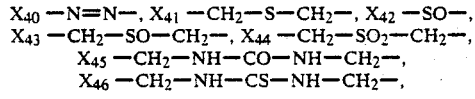
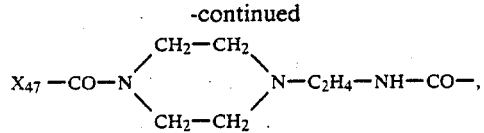
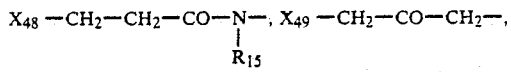
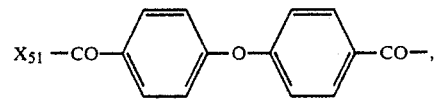
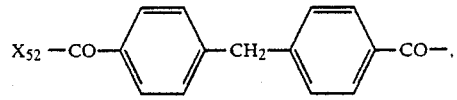
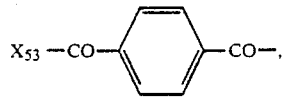
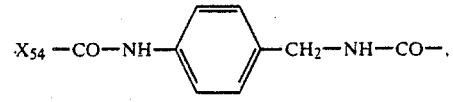
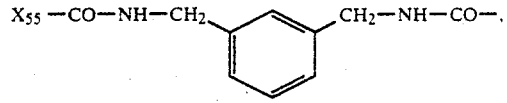
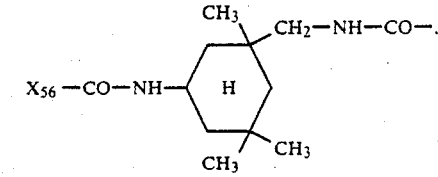
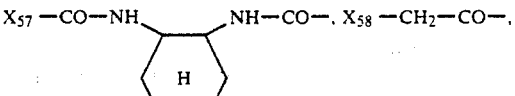
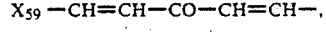
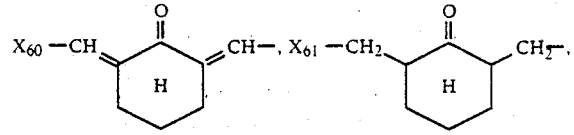
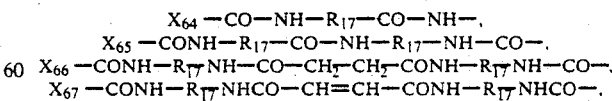
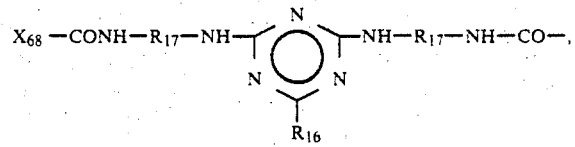

-continued

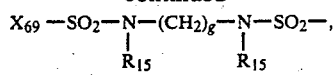

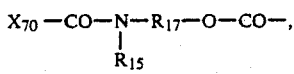

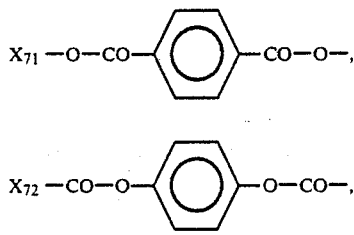

or,

X, when one $R_1$ is other than hydrogen, is $X_1$, $X_2$, $X_{14}$, $X_{21}$, $X_{32}$ or $X_{34}$, where $R_{14}$ is halogen, unsubstituted $C_{1-4}$alkyl and unsubstituted $C_{1-4}$alkoxy;

each $R_{15}$ independently is selected from hydrogen or unsubstituted $C_{1-4}$alkyl;

$R_{16}$ is selected from halogen, —OH, —NH$_2$, an aliphatic amine group, an aromatic amine group and a cycloaliphatic amine group;

each $R_{17}$ independently is a linear or branched unsubstituted $C_{1-4}$alkylene group;

each g independently is an integer from 1 to 4 inclusive;

or when the compounds of formula I are in 1:1 or 1:2 metal complex form, $R_1$ and $R_5$ (located on rings attached to the same azo group) form a group —O—Me—NH— or —O—Me—O— or $R_1$ and $R_{5a}$ (located on rings attached to the same azo group) form a group —O—Me—O—, where Me is a 1:1 or 1:2 complex-forming metal atom;

with the provisos:
(i) that the compounds of formula I have at least two basic water-solubilising groups; and
(ii) that X is attached in the 3- or 4-position of the phenyl ring.

The term "basic water-solubilising group" includes cationic groups and protonatable basic groups. Hence the minimum requirement for two water-solubilising basic groups may be made up of a cationic and a protonatable basic group or two protonatable basic groups or two cationic groups.

In this specification, unless indicated to the contrary, the significances of any symbol appearing more than once in a formula are independent of one another.

Preferably any halogen is chloro or bromo, more preferably the former; preferably any $C_{1-4}$alkyl is methyl or ethyl and preferably any $C_{1-4}$alkoxy is methoxy or ethoxy.

Preferably Me is iron, copper, cobalt, nickel, manganese or chromium in 1:1 metal complexes. Preferably Me is cobalt, chromium, nickel or iron in 1:2 metal complexes. More preferably Me is copper in 1:1 metal complexes and cobalt, chromium or iron in 1:2 metal complexes.

For the avoidance of doubt in 1:2 metal complexes according to the invention it is only necessary for one of the complexing azo compounds to be of formula I. The other complexing unit may or may not be a residue of a metal-free compound of formula I.

Preferably however both complexing units are residues of a metal-free compound of formula I. More preferably compounds of formula I are symmetric.

Preferred compounds of formula I are of formula I'

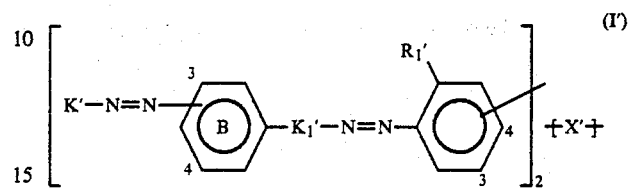

in metal-free or 1:1 or 1:2 metal complex form;

in which each $K_1'$ independently is selected from groups of formulae II' and III'

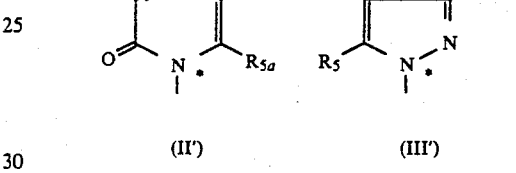

in which
the starred atom is attached to the phenyl ring;
$R_1'$ is hydrogen, Cl, methyl, methoxy or —OH, $R_5$ is —NH$_2$ or —OH and $R_{5a}$ is —OH; or $R_1'$ and $R_5$ form a group —O—Me—O— or —O—Me—NH; or $R_1'$ and $R_{5a}$ form a group —O—Me—O—;
$R_3'$ is —CH$_3$, —C$_2$H$_5$ or unsubstituted phenyl;
T' is hydrogen, —CN, —CONH$_2$ or

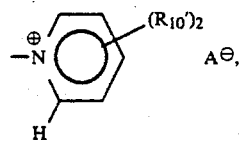

where
$R_{10}'$ is hydrogen, methyl, —NH$_2$, —N(CH$_3$)$_2$ or —CONH$_2$;
K' is a group of formulae Ka to Kg

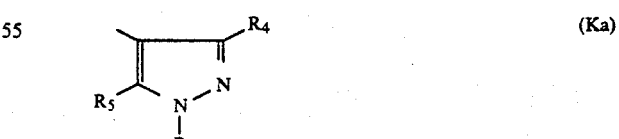

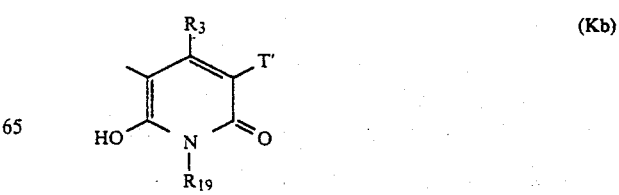

-continued

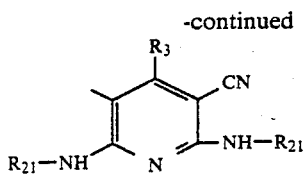

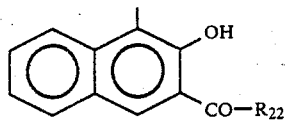

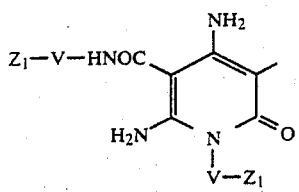

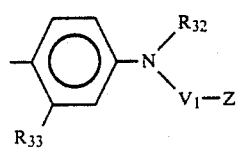

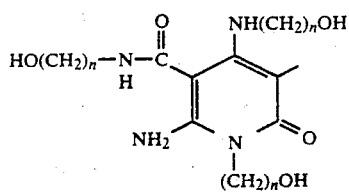

in which $R_{18}$ is hydrogen, unsubstituted $C_{1-4}$alkyl,

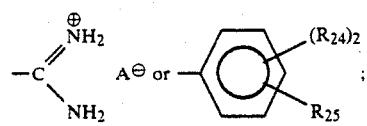

$R_{19}$ is hydrogen, unsubstituted $C_{1-6}$alkyl,

—NHCH$_3$; —NH$_2$; —NH—⌬, ($C_{1-4}$alkoxy)($C_{1-4}$alkyl), phenyl($C_{1-3}$alkyl), —(CH$_2$)$_{2-3}$—CN, —(CH$_2$)$_{2-3}$—OH,

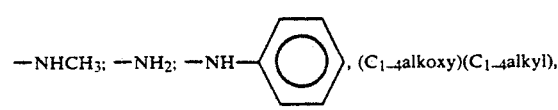

—(CH$_2$)$_m$—N(R$_{15}$)—CO—(CH$_2$)$_{1-2}$—Z,

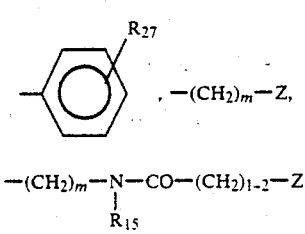 or

-continued

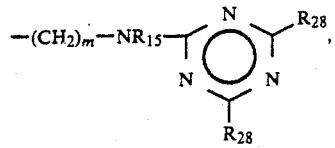

where
m is an integer from 1 to 6 inclusive;
n is an integer from 1 to 4 inclusive;
$R_{21}$ is hydrogen, $C_{1-4}$alkyl unsubstituted or monosubstituted by alkoxy (e.g., methoxy), —(CH$_2$)$_2$OH or —(CH$_2$)$_{2-3}$—Z;
$R_{22}$ is —NH(CH$_2$)$_m$—Z or

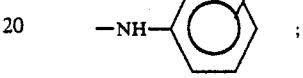 ;

$Z_1$ is —N(R$_{29}$)$_2$, —N$^\oplus$(R$_{30}$)$_2$R$_{31}$A$^\ominus$ or —OH;
Z is a group —N(R$_{29}$)$_2$ or —N$^\oplus$(R$_{30}$)$_2$R$_{31}$A$^\ominus$;
V is a linear $C_{1-12}$alkylene or $C_{3-12}$alkenylene group, the alkylene or alkenylene group of which may be interrupted by 1 or 2 heteroatoms (preferably $Z_a$ defined above);
$R_{24}$ is hydrogen, halogen, unsubstituted $C_{1-4}$alkyl, unsubstituted $C_{1-4}$alkoxy, —NO$_2$, —NH$_2$ or —NHCOCH$_3$;
$R_{25}$ is hydrogen, —NHCO(CH$_2$)$_{1-2}$—Z, —SO$_2$NH(CH$_2$)$_{2-3}$—Z or

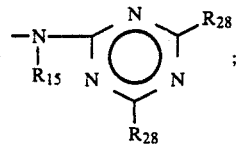 ;

$R_{27}$ is hydrogen, —NH$_2$, —NHCH$_3$, —N(CH$_3$)$_2$, —N(C$_2$H$_5$)$_2$, —NHCOCH$_3$, —NH—CO(CH$_2$)$_{1-2}$—Z,

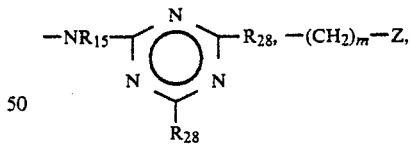

—SO$_2$—NH—(CH$_2$)$_m$—Z or 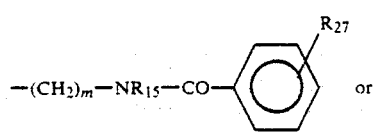 ;

$R_{28}$ is halogen, —OH, —NH$_2$, —NHC$_2$H$_4$OH, —N(C$_2$H$_4$OH)$_2$,

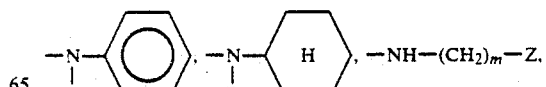

—NH(CH$_2$)$_{2-3}$—CN, —NH—(CH$_2$)$_{2-3}$—O—$C_{1-4}$alkyl or

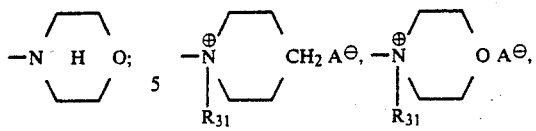

each R$_{29}$ independently is hydrogen, C$_{1-4}$alkyl unsubstituted or monosubstituted by a phenyl group or C$_{2-4}$alkyl monosubstituted by —OH, halogen or —CN or both R$_{29}$'s together with the N atom to which they are attached form an unsubstituted morpholine, piperidine, pyrrolidine, piperazine or N-methylpiperazine ring;

each R$_{30}$ independently has a significance of R$_{29}$ (independently of R$_{29}$) other than hydrogen and R$_{31}$ is C$_{1-4}$alkyl, unsubstituted or substituted by a phenyl group or both R$_{30}$'s and R$_{31}$ together with the N-atom to which they are attached form an unsubstituted pyridine, picoline or lutidine ring or

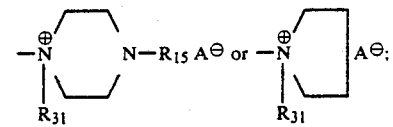

V$_1$ is linear unsubstituted C$_{1-4}$alkylene;

R$_{32}$ is hydrogen, —V$_1$—Z, or C$_{1-4}$alkyl unsubstituted or monosubstituted by —OH;

R$_{33}$ is hydrogen, unsubstituted C$_{1-4}$alkyl, —NHCOR$_7$ or —NHCO—V$_1$—Z, where R$_7$ is C$_{1-4}$alkyl;

X', when both R$_1$' s are hydrogen, is X$_1$, X$_5$, X$_6$, X$_7$, X$_{10}$, X$_{11}$, X$_{12}$, X$_{16}$, X$_{17}$, X$_{22}$, X$_{25}$, X$_{26}$, X$_{27}$, X$_{30}$, X$_{31}$, X$_{49}$, X$_{50}$, X$_{51}$, X$_{52}$, X$_{53}$, X$_{54}$, X$_{58}$, X$_{59}$, X$_{64}$, X$_{72}$ or,

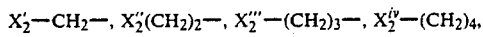

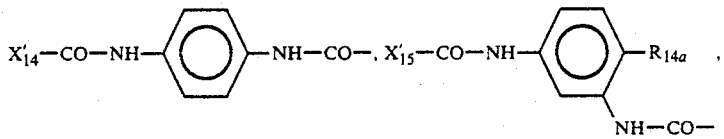

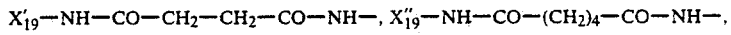

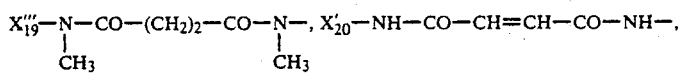

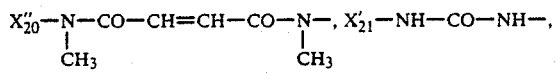

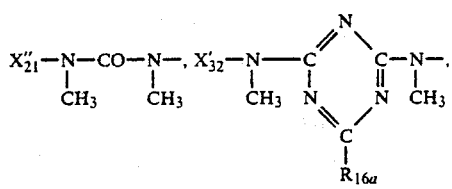

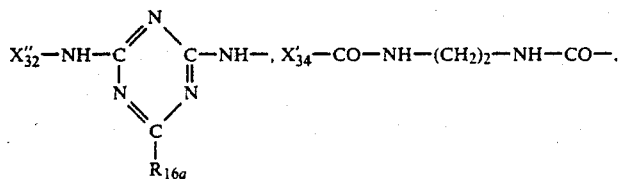

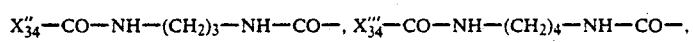

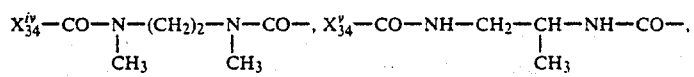

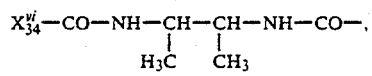

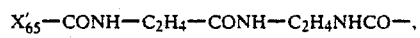

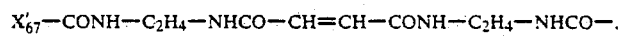

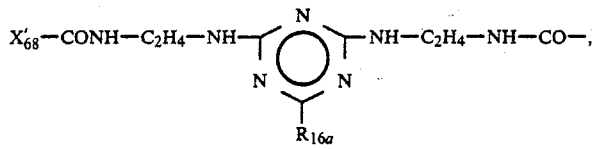

wherein
R$_{14a}$ is hydrogen, Cl, —CH$_3$ or —OCH$_3$; and
R$_{16a}$ is Cl, —OH, —NH$_2$, —NH—CH$_2$CH$_2$—OH, —NH(CH$_2$)$_3$N(C$_2$H$_5$)$_2$, —N(CH$_2$—CH$_2$OH)$_2$,

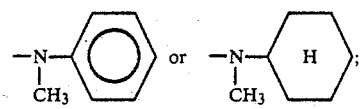

X', when one R$_1$' is other than hydrogen, is selected from X$_1$, X$_2$', X$_2$″, X$_{14}$', X$_{21}$', X$_{32}$″ and X$_{34}$';
with the provisos:
(i) that the azo group is in a 3- or 4-position of ring B;
(ii) that X' is attached in a 3- or 4-position to each phenyl ring; and
(iii) that in the compound of formula I' there are at least two water-solubilising basic groups present.

More preferred compounds of formula I are of formula I″

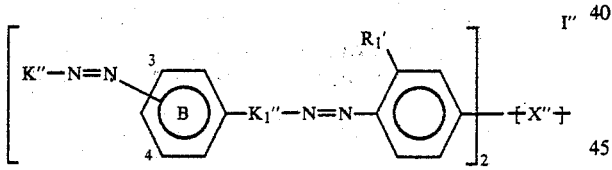

in metal-free or 1:1 or 1:2 metal complex form, in which K$_1$″ is of formula II″ or III'

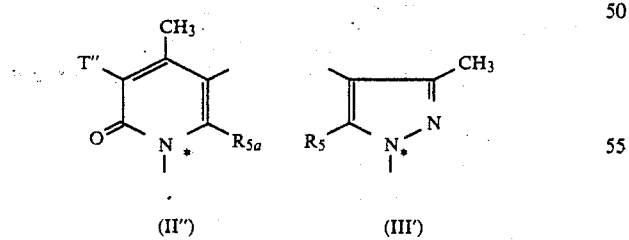

where
the starred atom is attached to the phenyl ring;
R$_1$' is hydrogen, Cl, methyl, methoxy or —OH, R$_5$ is —OH or —NH$_2$ and R$_{5a}$ is —OH or R$_1$' and R$_5$ form a group —O—Me$_1$—NH— or —O—Me$_1$—O— or R$_1$' and R$_{5a}$ form a group —O—Me$_1$—O—, where Me$_1$ is copper for 1:1 metal complexes and cobalt, chromium or iron for 1:2 metal complexes;
T″ is —CN or

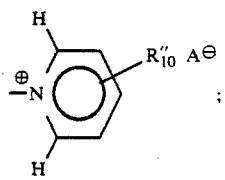

R$_{10}$″ is hydrogen, methyl or —NH$_2$
K″ is a group of one of the formulae Ka' to Kg'

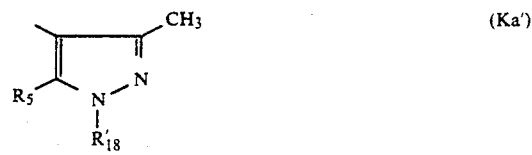 (Ka')

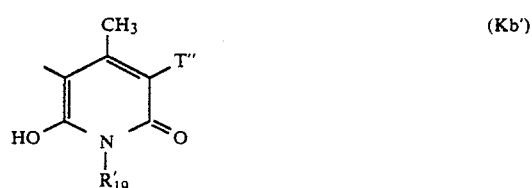 (Kb')

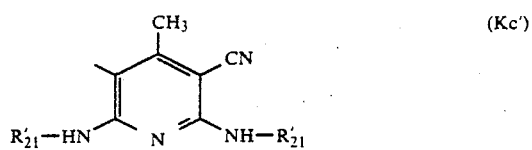 (Kc')

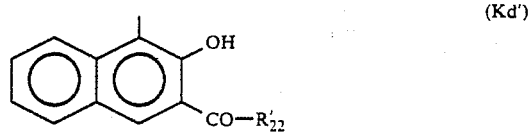 (Kd')

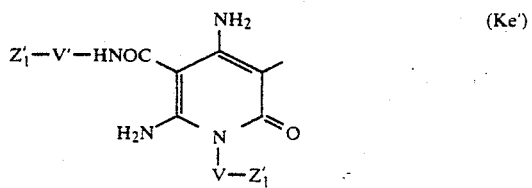 (Ke')

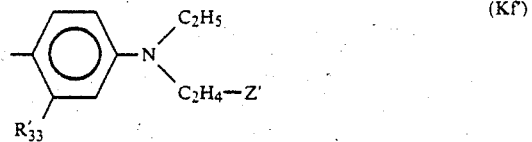 (Kf')

-continued

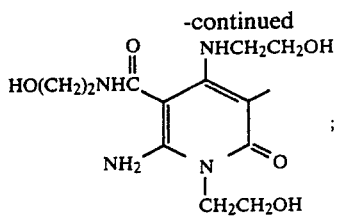

wherein
R$_{18}'$ is hydrogen,

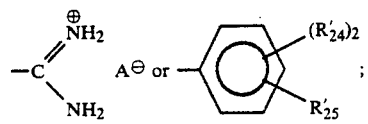

R$_{19}'$ is hydrogen, methyl, ethyl, benzyl,

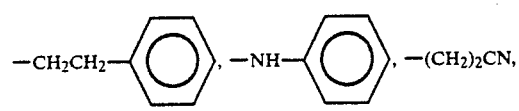

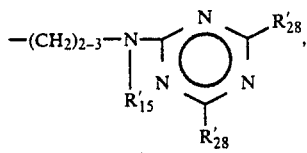

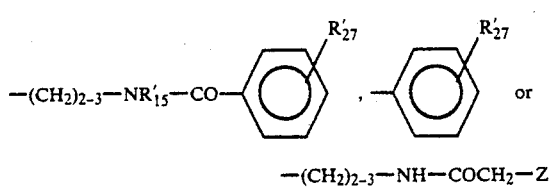

where
R$_{15}'$ is hydrogen or methyl;
R$_{21}'$ is hydrogen, methyl, ethyl, —(CH$_2$)$_2$OH, —(CH$_2$)$_3$—OCH$_3$, or —(CH$_2$)$_{2-3}$—Z';
R$_{22}'$ is —NH(CH$_2$)$_{2-3}$—Z' or

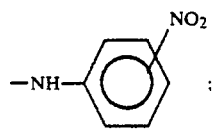

R$_{24}'$ is hydrogen, chloro, methyl, methoxy or —NHCOCH$_3$;
R$_{25}'$ is hydrogen, —NHCOCH$_2$—Z', —SO$_2$NH(CH$_2$)$_{2-3}$—Z'. or

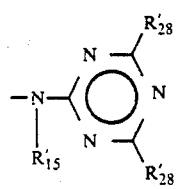

R$_{27}'$ is hydrogen, —NH$_2$, —N(CH$_3$)$_2$, —N(C$_2$H$_5$)$_2$, —NHCOCH$_3$, —NHCOCH$_2$—Z',

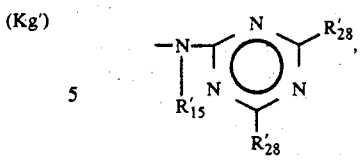

—(CH$_2$)$_{2-3}$—Z' or —SO$_2$NH(CH$_2$)$_{2-3}$—Z';
R$_{28}'$ is chloro, —OH, —NH$_2$,

—NHC$_2$H$_4$OH, —N(C$_2$H$_4$OH)$_2$, —NHC$_2$H$_4$CN, —NH(CH$_2$)$_3$OCH$_3$ or —NH—(CH$_2$)$_{2-3}$—Z',
Z$_1'$ is —N(R$_{29}'$)$_2$ or —OH;
Z' is —N(R$_{29}'$)$_2$ or —N$^⊕$(R$_{30}'$)$_2$R$_{31}'$A$^⊖$;
V' is —(CH$_2$)$_b$— where b is an integer from 2 to 6 inclusive;
R$_{29}'$ independently is hydrogen, methyl or ethyl or both R$_{29}'$s together with the N atom to which they are attached form an unsubstituted morpholine, piperidine, piperazine or N-methylpiperazine ring;
each R$_{30}'$ independently is methyl or ethyl and R$_{31}'$ is methyl, ethyl or benzyl or both R$_{30}'$s and R$_{31}'$ together with the N atom to which they are attached form an unsubstituted pyridine ring or a α- or β-picoline ring; and
R$_{33}'$ is hydrogen, methyl, —NHCOCH$_3$, —NHCOC$_2$H$_5$ or —NHCO(CH$_2$)$_{2-3}$—Z';
X''', when both R$_1'$s are hydrogen, is X$_1$, X$_{11}$, X$_{17}$, X$_{27}$, X$_{51}$, X$_{52}$, X$_{54}$, X$_{64}$, X$_{72}$, X$_2'$, X$_2''$, X$_{14}'$, X$_{19}'$, X$_{19}''$, X$_{19}'''$, X$_{20}'$, X$_{20}''$, X$_{32}'$, X$_{32}''$, X$_{34}'$, X$_{34}''$, X$_{34}'''$, X$_{34}^{iv}$, X$_{34}^v$, X$_{34}^{vi}$, X$_{67}'$ and X$_{68}'$; and when one of R$_1'$ is other than hydrogen, X''' is a direct bond;
with the provisos:
(i) that in the compound of formula I'' there are at least two basic water-solubilising groups; and
(ii) that the azo group is in the 3- or 4-position of ring B.

In compounds according to the invention:
preferably q is 0;
preferably K$_1$ is K$_1'$, more preferably K$_1''$;
preferably R$_1$ is R$_1'$;
preferably R$_3$ is R$_3'$, more preferably CH$_3$;
preferably R$_4$ is CH$_3$;
preferably T is T', more preferably T'';
preferably R$_{10}$ is R$_{10}'$, more preferably R$_{10}''$;
preferably R$_{12}$ is hydrogen or methyl, more preferably the latter;
preferably K is K', more preferably K'';
preferably X is X', more preferably X'';
preferably R$_{14}$ is R$_{14a}$;
preferably R$_{15}$ is hydrogen or methyl;
preferably R$_{16}$ is R$_{16a}$;
preferably g is 2, 3 or 4;
preferably R$_{17}$ is —(CH$_2$)$_{2-3}$—.
preferably R$_{18}$ is R$_{18}'$;
preferably R$_{19}$ is R$_{19}'$;
preferably R$_{21}$ is R$_{21}'$;
preferably R$_{22}$ is R$_{22}'$;
preferably R$_{24}$ is R$_{24}'$;
preferably R$_{25}$ is R$_{25}'$;
preferably R$_{27}$ is R$_{27}'$;

preferably R$_{28}$ is R$_{28}$';
preferably R$_{29}$ is R$_{29}$';
preferably R$_{30}$ is R$_{30}$';
preferably R$_{31}$ is R$_{31}$';
preferably R$_{33}$ is R$_{33}$';
preferably Z is Z';
preferably Z$_1$ is Z$_1$';
preferably V is V'; and
preferably V$_1$ is —(CH$_2$)$_{2-3}$.

R$_{16}$, when an aliphatic amine, is preferably of the formula

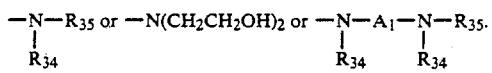

where
R$_{34}$ is hydrogen or C$_{1-4}$alkyl; R$_{35}$ is C$_{1-4}$alkyl unsubstituted or monosubstituted by —OH and A$_1$ is a linear or branched C$_{1-4}$alkylene. More preferably R$_{16}$ when an aliphatic amine, is —NHCH$_2$CH$_2$OH, —N(CH$_2$CH$_2$OH)$_2$ or —NH—(CH$_2$)$_3$—N(C$_2$H$_5$)$_2$;

R$_{16}$, when an aromatic amine, is preferably

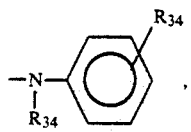, more preferably

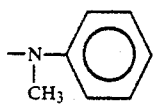.

R$_{16}$, when a cycloaliphatic amine, is preferably

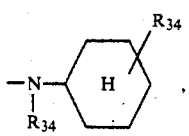, more preferably

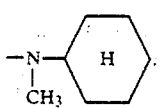.

R$_{19}$, when phenyl(C$_{1-3}$alkyl), is preferably

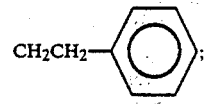;

R$_{19}$, when alkoxyalkyl, is preferably —(CH$_2$)$_3$—OCH$_3$.

V, when an alkylene group, is preferably —(CH$_2$)$_2$—.

R$_{28}$, when —NH—(CH$_2$)$_{2-3}$—OC$_{1-4}$alkyl, is preferably —NH(CH$_2$)$_3$OCH$_3$.

R$_{30}$, when an alkyl group substituted by phenyl, is preferably benzyl.

Compounds of formula I in metal-free form may be prepared by reacting 1 mole of a tetrazotised compound of formula VI

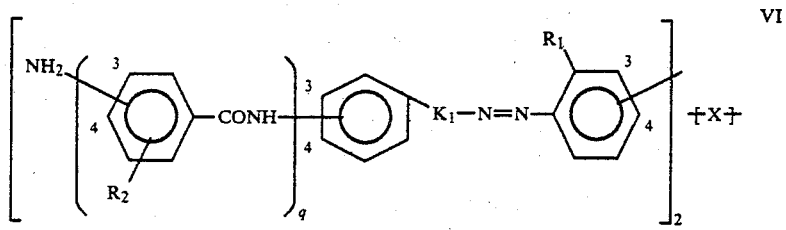

with the proviso that the —NH$_2$ group and X group are in the 3- or 4-position on their respective phenyl rings
with 2 moles of a compound of formula VII

H—K          (VII)

The diazo coupling can be carried out according to known methods. Advantageously, coupling is carried out in aqueous, acid, neutral or alkali medium at a temperature from −10° C. to room temperature, if necessary in the presence of a coupling accelerator such as pyridine or urea. Alternatively, coupling may be effected in a mixture of solvents, for example water and an organic solvent.

The azo compounds of formula I in 1:1 metal complex form may be prepared by metallising compounds of formula I in metal-free form with a metal selected from copper, cobalt, iron, nickel, manganese, chromium and zinc.

The azo compounds of formula I in 1:2 metal complex form may be prepared by metallising compounds of formula I in metal-free form with metal selected from chromium, nickel, cobalt and iron.

A further method for the preparation of an azo compound of formula I in 1:2 metal complex form is bonding an azo compound of formula I in metal-free form (or a metallisable azo compound of a formula other than formula I) with an azo compound of formula I in 1:1 metal complex form when the metal is chromium, nickel, cobalt or iron.

The metallisation process to form a 1:1 metal complex is advantageously carried out by treating 1 mole of azo compound with a metallising agent containing 1 equivalent of metal.

Metallisation is carried out by known methods, by metallising at a pH range of preferably 2 to 7 with the metal salt or by oxidatively coppering preferably at pH 4 to 7 in the presence of the copper salt and an oxidation agent (H$_2$O$_2$, for example) or by demethylatively coppering or cobaltising preferably at pH 3 to 4 at a raised temperature in the presence of a metal salt.

Advantageously, for instance, cobaltisation may be carried out in the presence of an inorganic nitrite such as lithium, sodium, ammonium or potassium nitrite in the ratio of 2 to 6 moles of nitrite per gram atom of cobalt.

Suitable cobalt-yielding compounds are, for example, cobalt (II) and Co (III) sulphate, acetate, formate or chloride.

Copper-yielding compounds are, for example, cupric sulphate, cupric formate, cupric acetate and cupric chloride.

Suitable nickel-yielding compounds are Ni(II) and Ni(III) compounds, such as nickel formate, nickel acetate and nickel sulphate.

Suitable manganese-yielding compounds are Mn(II) compounds and iron-yielding compounds are Fe(II) and Fe(III) compounds. Examples of these and zinc-yielding compounds are manganese, iron and zinc formate, acetate and sulphate.

Suitable chromium-yielding compounds are Cr(II) and Cr(III) formate, acetate and sulphate.

Compounds of formula VI are known or may be prepared by known methods from known compounds.

Compounds of formula VII are known or may be made from known compounds by known methods except when K is a group of formula Ke and Kg (defined under K'). An example of the formation of a compound of formula VII when K is a group of formula Kb and $R_{19}$ is a group —$(CH_2)_2$—$NH_2$ (defined under K') is given below.

A compound of the formula VIII

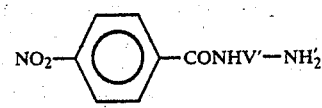

(VIII)

where V' is —$C_2H_4$— can be formed by the reaction of a paranitrobenzoic acid aryl ester with ethylenediamine. The compound of formula VIII is then reacted with chloroacetic acid methyl ester and then with pyridine according to known methods to form a compound of formula IX

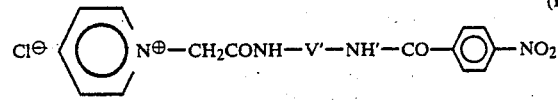

(IX)

Acetoacetic acid methyl ester is added to the compound of formula IX at 25° C. in the presence of NaOH causing it to cyclise to form a compound of formula X

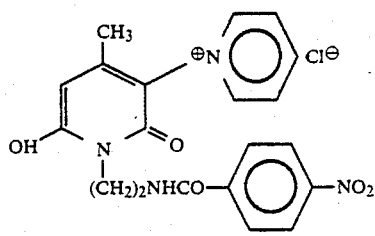

(X)

The compound of formula X can be saponified by the addition of 5 to 7% HCl to give an amine of formula XI

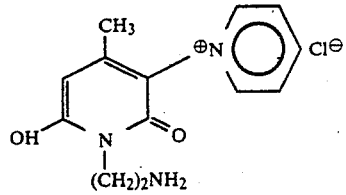

(XI)

Compounds of formula VII in which K is Ke can be prepared by cyclising 2 moles of a compound of the formula XIa $$Z_1—V—NHCOCH_2—CN \qquad (XIa)$$

for example in practically water-free organic solvent (such as an alcohol) at elevated temperatures in the presence of a base (such as an alcoholate). The compounds of formula XIa are known or may be prepared by known methods from known compounds.

Compounds of formula VII in which K is Kg (defined under K') can be prepared by reacting cyanoacetic ester with an amino alcohol and, without isolation of the cyanoacetic acid amide, cyclising at raised temperatures in the presence of a strong base, for example an alcoholate.

The anion $A^\ominus$ may be any non-chromophoric anion which is usual in basic dyestuff chemistry.

In the compounds of formula I, any anion $A^\ominus$ may be exchanged for any other non-chromophoric anion, e.g. with the aid of an ion exchanger, or by means of a reaction with salts or acids, optionally in several stages, e.g. through the hydroxide or the bicarbonate, or in accordance with German Published Specification No. 2,001,748 or 2,001,816.

The anion $A^\ominus$ includes both organic and inorganic ions, e.g. halide (such as chloride or bromide), sulphate, bisulphate, methylsulphate, aminosulphonate, perchlorate, benzenesulphonate, oxalate, maleinate, acetate, propionate, lactate, succinate, tartrate, malate, methanesulphonate and benzoate ions, complex anions (such as those of zinc chloride double salts) and the anions of the following acids: boric acid, citric acid, glycolic acid, diglycolic acid and adipic acid, or addition products of ortho-boric acid with polyalcohols, e.g. cis-polyols.

The compounds of formula I in quaternised form and/or in the form of the corresponding salts of mineral acids or organic acids may be used directly as dyestuffs. They may be used in the form of aqueous stable solutions or as granules and may be used for dyeing all types of fibre material, cellulose, cotton and leather, especially paper and paper products, and bast fibres, such as hemp, flax, sisal, jute, coir and straw.

The compounds of formula I may also be employed in the production of bulk-dyed, sized and unsized paper. They may be similarly employed for dyeing paper by dipping.

Paper, leather and cellulose are dyed in accordance with known methods.

In paper production, the compounds of formula I and their preparations do not colour the waste water at all, or only slightly which is particularly useful for purifying waste water. Compounds of formula I are highly substantive, do not give mottled dyeings when dyed on paper, and are substantially insensitive to pH. The dyeings on paper are notable for their good light fastness properties. After long-term exposure to light, the shade alters tone-in-tone. The dyed papers are wetfast, not only to water, but also to milk, soap water, sodium chloride solutions, fruit juices and sweetened mineral water, and because of their good alcohol fastness, they are also resistant to alcoholic beverages. Furthermore, when dyed on paper, they produce dyeings having a very stable shade.

The compounds of formula I may be used for dyeing, padding or printing polyacrylonitrile textiles, or polyamide or polyester textiles which are modified by anionic groups.

In the following Examples, all parts and percentages are by weight and all temperatures are given in degrees Centigrade unless indicated to the contrary.

EXAMPLE 1

15 Parts of N,N'-(bis-para-aminobenzoyl)ethylenediamine are suspended in 150 parts of water and 25 parts of 10N hydrochloric acid. 25 Parts of a 4N sodium nitrite solution are added over the course of 20 minutes at a temperature of between 0° and 5°. After the addition of the nitrite, the residual nitrous acid is destroyed with aminosulphonic acid. The diazonium salt solution formed is filtered by adding decolourising carbon.

This solution is then added dropwise over 30 minutes at 10° and 15° to a coupling solution containing hydrochloric acid, and 20 parts of 1-(3'-aminophenyl)-3-methyl-5-hydroxypyrazole. During this addition, the pH value is kept at between 2.5 and 3.5 by adding simultaneously a solution of caustic soda. When coupling has ended, the reaction mixture is rendered alkaline with ammonia solution, and the dyestuff suspension is heated to 60°. After cooling, it is filtered and washed with water. The bisazo dyestuff thus obtained is suspended in hydrochloric acid, is bisdiazotised in a manner analogous to that described above using sodium nitrite, and is coupled at a pH value of 2 to 3 with the coupling component 1-(3'-dimethylaminopropyl)-3-pyridinium-4-methyl-6-hydroxy-1,2-dihydropyrid-2-one chloride, which is in a slightly acidic solution containing hydrochloric acid. After coupling, the dyestuff is isolated by addition of ammonia and filtering the resulting suspension. The dyestuff so obtained has the formula

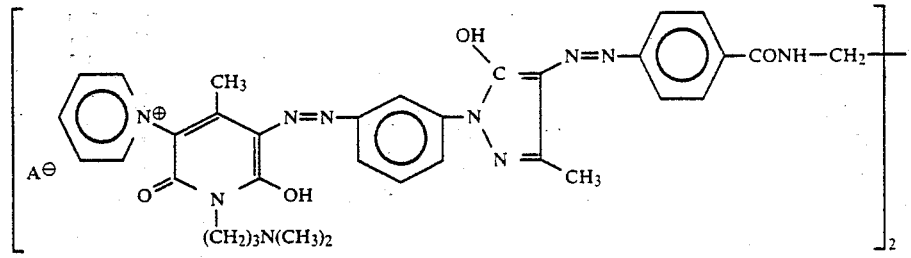

and when in a slightly acidic solution, dyes cotton, leather and paper yellow. The paper dyeings have good light fastness and very good wet fastness.

In the following Tables the significances of X (i.e. as any one of $X_1$ to $X_{73}$) are as given earlier in the specification.

$K_1$ is 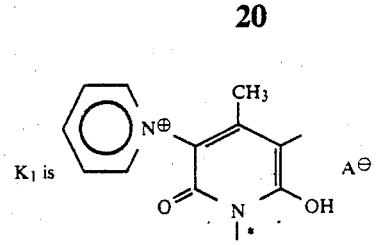

$K_2$ is 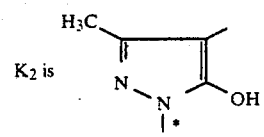

$K_3$ is 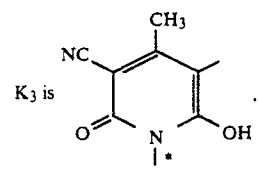

wherein the starred atom is bound to the ring G;

$T_1$ is 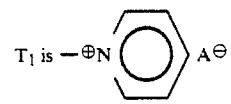

$T_2$ is 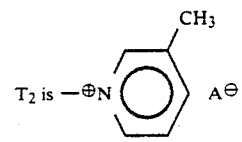

$T_3$ is 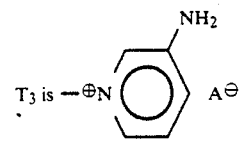

$T_4$ is 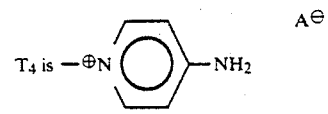

$T_5$ is 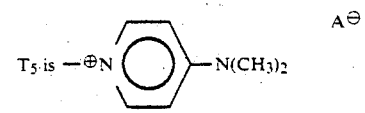

-continued $T_6$ is 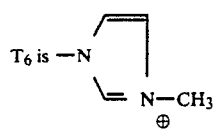 $A^\ominus$ $T_7$ is 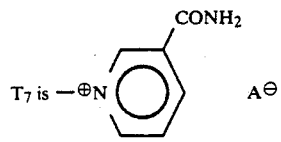 $A^\ominus$ $T_8$ is —CN
$A_1$ is —(CH$_2$)$_3$N(CH$_3$)$_2$
$A_2$ is —(CH$_2$)$_3$N$^\oplus$(CH$_3$)$_3$ $A^\ominus$
$A_3$ is H
$A_4$ is —(CH$_2$)$_3$OCH$_3$ $A_5$ is —CH$_2$—CH$_2$— 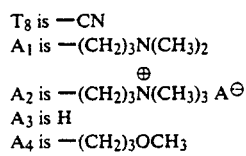

$A_6$ is 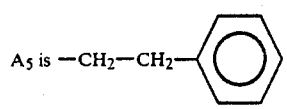

$A_7$ is 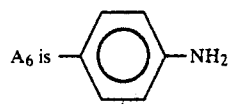

$A_8$ is 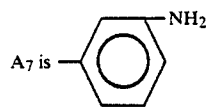

$A_9$ is  $A^\ominus$ $A_{10}$ is 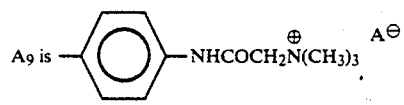 $A^\ominus$ $A_{11}$ is 

$A_{12}$ is 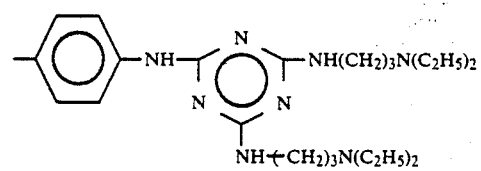

$A_{13}$ is —C$_2$H$_4$NH$_2$ $A_{14}$ is 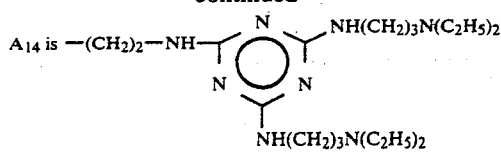

$A_{15}$ is 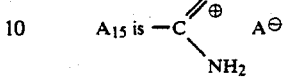 $A^\ominus$

EXAMPLES 2 TO 145

Compounds of the formula

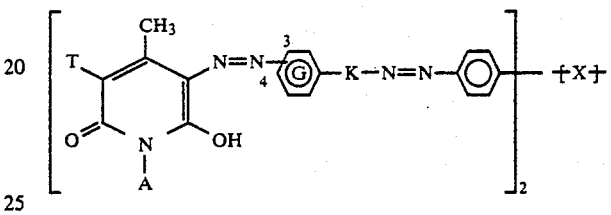

wherein A, T, KI, X and G are defined in Table I, can be prepared by a method analogous to that of Example 1 from appropriate starting materials.

TABLE I

| EX. No. | K | Position of azo group on Ring G | T | A | X |
|---|---|---|---|---|---|
| 2 | $K_2$ | 3 | $T_1$ | $A_2$ | $X_{34}'$ |
| 3 | $K_2$ | 3 | $T_2$ | $A_3$ | " |
| 4 | $K_2$ | 3 | $T_1$ | $A_3$ | " |
| 5 | $K_2$ | 3 | $T_3$ | $A_3$ | " |
| 6 | $K_2$ | 3 | $T_4$ | $A_3$ | " |
| 7 | $K_2$ | 3 | $T_5$ | $A_3$ | " |
| 8 | $K_2$ | 3 | $T_6$ | $A_3$ | " |
| 9 | $K_2$ | 3 | $T_7$ | $A_3$ | " |
| 10 | $K_2$ | 3 | $T_1$ | $A_4$ | " |
| 11 | $K_2$ | 3 | $T_1$ | $A_5$ | " |
| 12 | $K_2$ | 3 | $T_1$ | $A_6$ | " |
| 13 | $K_2$ | 3 | $T_1$ | $A_7$ | " |
| 14 | $K_2$ | 3 | $T_1$ | $A_8$ | " |
| 15 | $K_2$ | 3 | $T_1$ | $A_9$ | " |
| 16 | $K_2$ | 3 | $T_1$ | $A_{10}$ | " |
| 17 | $K_2$ | 3 | $T_1$ | $A_{11}$ | " |
| 18 | $K_2$ | 3 | $T_1$ | $A_{12}$ | " |
| 19 | $K_2$ | 3 | $T_1$ | $A_{13}$ | " |
| 20 | $K_2$ | 3 | $T_1$ | $A_{14}$ | " |
| 21 | $K_2$ | 3 | $T_8$ | $A_{14}$ | " |
| 22 | $K_2$ | 3 | $T_8$ | $A_1$ | " |
| 23 | $K_2$ | 3 | $T_8$ | $A_9$ | " |
| 24 | $K_2$ | 3 | $T_8$ | $A_{10}$ | " |
| 25 | $K_2$ | 3 | $T_8$ | $A_{11}$ | " |
| 26 | $K_2$ | 3 | $T_8$ | $A_{12}$ | " |
| 27 | $K_2$ | 4 | $T_1$ | $A_1$ | " |
| 28 | $K_2$ | 4 | $T_2$ | $A_3$ | " |
| 29 | $K_2$ | 4 | $T_4$ | $A_3$ | " |
| 30 | $K_2$ | 4 | $T_7$ | $A_3$ | " |
| 31 | $K_2$ | 4 | $T_1$ | $A_9$ | " |
| 32 | $K_2$ | 4 | $T_1$ | $A_{10}$ | " |
| 33 | $K_2$ | 4 | $T_1$ | $A_{11}$ | " |
| 34 | $K_2$ | 4 | $T_1$ | $A_{12}$ | " |
| 35 | $K_2$ | 4 | $T_1$ | $A_{14}$ | " |
| 36 | $K_2$ | 4 | $T_8$ | $A_{11}$ | " |
| 37 | $K_2$ | 4 | $T_8$ | $A_{12}$ | " |
| 38 | $K_3$ | 3 | $T_1$ | $A_1$ | " |
| 39 | $K_3$ | 3 | $T_1$ | $A_2$ | " |
| 40 | $K_3$ | 3 | $T_1$ | $A_3$ | " |
| 41 | $K_3$ | 3 | $T_3$ | $A_3$ | " |
| 42 | $K_3$ | 3 | $T_5$ | $A_3$ | " |
| 43 | $K_3$ | 3 | $T_6$ | $A_3$ | " |
| 44 | $K_3$ | 3 | $T_1$ | $A_9$ | " |
| 45 | $K_3$ | 3 | $T_1$ | $A_{10}$ | " |

TABLE I-continued

| EX. No. | K | Position of azo group on Ring G | T | A | X |
|---|---|---|---|---|---|
| 46 | $K_3$ | 3 | $T_1$ | $A_1$ | " |
| 47 | $K_3$ | 3 | $T_1$ | $A_{12}$ | " |
| 48 | $K_3$ | 3 | $T_1$ | $A_{13}$ | " |
| 49 | $K_3$ | 3 | $T_1$ | $A_{14}$ | " |
| 50 | $K_3$ | 3 | $T_8$ | $A_{14}$ | " |
| 51 | $K_3$ | 3 | $T_8$ | $A_1$ | " |
| 52 | $K_3$ | 3 | $T_8$ | $A_9$ | " |
| 53 | $K_3$ | 3 | $T_8$ | $A_{10}$ | " |
| 54 | $K_3$ | 3 | $T_8$ | $A_{11}$ | " |
| 55 | $K_3$ | 3 | $T_8$ | $A_{12}$ | " |
| 56 | $K_3$ | 4 | $T_1$ | $A_1$ | " |
| 57 | $K_3$ | 4 | $T_1$ | $A_3$ | " |
| 58 | $K_3$ | 4 | $T_5$ | $A_3$ | " |
| 59 | $K_3$ | 4 | $T_1$ | $A_9$ | " |
| 60 | $K_3$ | 4 | $T_1$ | $A_{12}$ | " |
| 61 | $K_3$ | 4 | $T_1$ | $A_{14}$ | " |
| 62 | $K_3$ | 4 | $T_8$ | $A_{14}$ | " |
| 63 | $K_3$ | 4 | $T_8$ | $A_{10}$ | " |
| 64 | $K_3$ | 4 | $T_8$ | $A_{12}$ | " |
| 65 | $K_1$ | 3 | $T_1$ | $A_1$ | " |
| 66 | $K_1$ | 3 | $T_1$ | $A_3$ | " |
| 67 | $K_1$ | 3 | $T_5$ | $A_3$ | " |
| 68 | $K_1$ | 3 | $T_4$ | $A_3$ | " |
| 69 | $K_1$ | 3 | $T_5$ | $A_3$ | " |
| 70 | $K_1$ | 3 | $T_6$ | $A_3$ | " |
| 71 | $K_1$ | 3 | $T_7$ | $A_3$ | " |
| 72 | $K_1$ | 3 | $T_1$ | $A_4$ | " |
| 73 | $K_1$ | 3 | $T_1$ | $A_5$ | " |
| 74 | $K_1$ | 3 | $T_1$ | $A_6$ | " |
| 75 | $K_1$ | 3 | $T_1$ | $A_7$ | " |
| 76 | $K_1$ | 3 | $T_1$ | $A_8$ | " |
| 77 | $K_1$ | 3 | $T_1$ | $A_9$ | " |
| 78 | $K_1$ | 3 | $T_1$ | $A_{10}$ | " |
| 79 | $K_1$ | 3 | $T_1$ | $A_{11}$ | " |
| 80 | $K_1$ | 3 | $T_1$ | $A_{12}$ | " |
| 81 | $K_1$ | 3 | $T_1$ | $A_{13}$ | " |
| 82 | $K_1$ | 3 | $T_1$ | $A_4$ | " |
| 83 | $K_1$ | 3 | $T_8$ | $A_{14}$ | " |
| 84 | $K_1$ | 3 | $T_8$ | $A_3$ | " |
| 85 | $K_1$ | 3 | $T_8$ | $A_1$ | " |
| 86 | $K_1$ | 3 | $T_8$ | $A_9$ | " |
| 87 | $K_1$ | 3 | $T_8$ | $A_{10}$ | " |
| 88 | $K_1$ | 3 | $T_8$ | $A_{11}$ | " |
| 89 | $K_1$ | 3 | $T_8$ | $A_{12}$ | " |
| 90 | $K_1$ | 3 | $T_8$ | $A_6$ | " |
| 91 | $K_1$ | 4 | $T_1$ | $A_1$ | " |
| 92 | $K_1$ | 4 | $T_2$ | $A_3$ | " |
| 93 | $K_1$ | 4 | $T_3$ | $A_3$ | " |
| 94 | $K_1$ | 4 | $T_1$ | $A_8$ | " |
| 95 | $K_1$ | 4 | $T_1$ | $A_{10}$ | " |
| 96 | $K_1$ | 4 | $T_1$ | $A_{12}$ | " |
| 97 | $K_1$ | 4 | $T_1$ | $A_{13}$ | " |
| 98 | $K_1$ | 4 | $T_8$ | $A_3$ | " |
| 99 | $K_1$ | 4 | $T_8$ | $A_1$ | " |
| 100 | $K_1$ | 4 | $T_8$ | $A_{10}$ | " |
| 101 | $K_1$ | 4 | $T_8$ | $A_{12}$ | " |
| 102 | $K_1$ | 3 | $T_1$ | $A_7$ | $X_{11}$ |
| 103 | $K_1$ | 4 | $T_1$ | $A_8$ | " |
| 104 | $K_1$ | 3 | $T_4$ | $A_3$ | " |
| 105 | $K_2$ | 3 | $T_1$ | $A_1$ | " |
| 106 | $K_2$ | 3 | $T_1$ | $A_{10}$ | " |
| 107 | $K_2$ | 3 | $T_1$ | $A_{12}$ | " |
| 108 | $K_2$ | 3 | $T_1$ | $A_{14}$ | " |
| 109 | $K_2$ | 3 | $T_8$ | $A_{14}$ | " |
| 110 | $K_3$ | 3 | $T_1$ | $A_1$ | " |
| 111 | $K_3$ | 3 | $T_8$ | $A_{12}$ | " |
| 112 | $K_1$ | 3 | $T_1$ | $A_3$ | $X_2'$ |
| 113 | $K_1$ | 4 | $T_1$ | $A_3$ | " |
| 114 | $K_1$ | 3 | $T_4$ | $A_3$ | " |
| 115 | $K_3$ | 3 | $T_1$ | $A_1$ | " |
| 116 | $K_3$ | 3 | $T_1$ | $A_{10}$ | " |
| 117 | $K_3$ | 3 | $T_1$ | $A_{12}$ | " |
| 118 | $K_3$ | 3 | $T_1$ | $A_{14}$ | " |
| 119 | $K_3$ | 3 | $T_8$ | $A_{12}$ | " |
| 120 | $K_2$ | 3 | $T_1$ | $A_1$ | " |
| 121 | $K_2$ | 3 | $T_8$ | $A_{12}$ | " |
| 122 | $K_1$ | 3 | $T_1$ | $A_3$ | $X_2''$ |
| 123 | $K_2$ | 3 | $T_1$ | $A_1$ | " |
| 124 | $K_3$ | 3 | $T_1$ | $A_1$ | " |
| 125 | $K_2$ | 3 | $T_8$ | $A_{12}$ | " |
| 126 | $K_3$ | 3 | $T_8$ | $A_{12}$ | " |
| 127 | $K_1$ | 3 | $T_1$ | $A_3$ | " |
| 128 | $K_1$ | 3 | $T_1$ | $A_3$ | $X_{21}'$ |
| 129 | $K_1$ | 3 | $T_1$ | $A_3$ | $X_{19}'$ |
| 130 | $K_1$ | 3 | $T_1$ | $A_3$ | $X_{67}'$ |
| 131 | $K_1$ | 3 | $T_1$ | $A_3$ | $X_{68}'$ |
| 132 | $K_1$ | 3 | $T_1$ | $A_3$ | $X_{72}$ |
| 133 | $K_2$ | 3 | $T_1$ | $A_1$ | $X_{67}'$ |
| 134 | $K_3$ | 3 | $T_1$ | $A_1$ | $X_{68}'$ |
| 135 | $K_3$ | 3 | $T_8$ | $A_{12}$ | $X_{67}'$ |
| 136 | $K_3$ | 3 | $T_8$ | $A_{12}$ | $X_{68}'$ |
| 137 | $K_2$ | 3 | $T_8$ | $A_{12}$ | $X_{72}$ |
| 138 | $K_2$ | 4 | $T_1$ | $A_1$ | $X_{11}$ |
| 139 | $K_2$ | 3 | $T_1$ | $A_1$ | " |
| 140 | $K_2$ | 4 | $T_1$ | $A_1$ | $X_{34}'$ |
| 141 | $K_2$ | 3 | $T_1$ | $A_1$ | " |
| 142 | $K_2$ | 4 | $T_1$ | $A_1$ | $X_2''$ |
| 143 | $K_2$ | 3 | $T_1$ | $A_1$ | " |
| 144 | $K_2$ | 4 | $T_1$ | $A_1$ | $X_2'$ |
| 145 | $K_2$ | 3 | $T_1$ | $A_1$ | " |

In Examples 131, 134, 136, where $X = X_{68}'$, $R_{16a}$ is $-NHC_2H_4OH$.

EXAMPLES 146 TO 181

Compounds of the formula

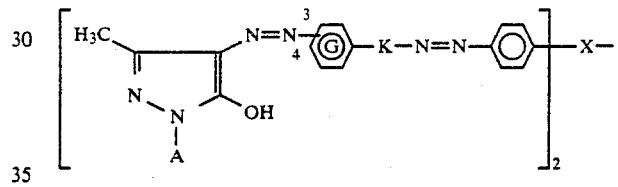

wherein A, K, X and G are defin in Table II and anion $A^\ominus$ is $Cl^\ominus$, may be prepared by a method analogous to that of Example 1 from appropriate starting materials.

TABLE II

| EX. No. | K | Position of azo group on Ring G | A | X |
|---|---|---|---|---|
| 146 | $K_2$ | 3 | $A_{15}$ | $X_{34}'$ |
| 147 | $K_2$ | 3 | $A_{10}$ | " |
| 148 | $K_2$ | 3 | $A_9$ | " |
| 149 | $K_2$ | 3 | $A_{11}$ | " |
| 150 | $K_2$ | 3 | $A_{12}$ | " |
| 151 | $K_2$ | 4 | $A_{11}$ | " |
| 152 | $K_2$ | 4 | $A_{12}$ | " |
| 153 | $K_3$ | 3 | $A_{10}$ | " |
| 154 | $K_3$ | 3 | $A_9$ | " |
| 155 | $K_3$ | 3 | $A_{11}$ | " |
| 156 | $K_3$ | 3 | $A_{12}$ | " |
| 157 | $K_3$ | 3 | $A_{15}$ | " |
| 158 | $K_3$ | 4 | $A_9$ | " |
| 159 | $K_3$ | 4 | $A_{11}$ | " |
| 160 | $K_3$ | 4 | $A_{12}$ | " |
| 161 | $K_1$ | 3 | $A_{10}$ | " |
| 162 | $K_1$ | 3 | $A_9$ | " |
| 163 | $K_1$ | 3 | $A_{11}$ | " |
| 164 | $K_1$ | 3 | $A_{12}$ | " |
| 165 | $K_1$ | 3 | $A_{15}$ | " |
| 166 | $K_1$ | 3 | $A_7$ | " |
| 167 | $K_1$ | 4 | $A_{10}$ | " |
| 168 | $K_1$ | 4 | $A_{11}$ | " |
| 169 | $K_1$ | 4 | $A_{15}$ | " |
| 170 | $K_2$ | 3 | $A_{10}$ | $X_{11}$ |
| 171 | $K_2$ | 3 | $A_{12}$ | " |
| 172 | $K_3$ | 3 | $A_{12}$ | " |
| 173 | $K_3$ | 3 | $A_{10}$ | $X_2'$ |
| 174 | $K_3$ | 3 | $A_{12}$ | " |
| 175 | $K_2$ | 3 | $A_{12}$ | " |
| 176 | $K_2$ | 3 | $A_{12}$ | $X_2''$ |
| 177 | $K_3$ | 3 | $A_{12}$ | " |

TABLE II-continued

| EX. No. | K | Position of azo group on Ring G | A | X |
|---|---|---|---|---|
| 178 | $K_2$ | 3 | $A_{12}$ | $X_{21}'$ |
| 179 | $K_2$ | 3 | $A_{12}$ | $X_{67}'$ |
| 180 | $K_2$ | 3 | $A_{12}$ | $X_{68}'$ |
| 181 | $K_2$ | 3 | $A_{12}$ | $X_{72}$ |

In Example 180 where X is $X_{68}'$ $R_{16a}$ is —$NHC_2H_4OH$.

EXAMPLES 182 TO 202

Compounds of the formula

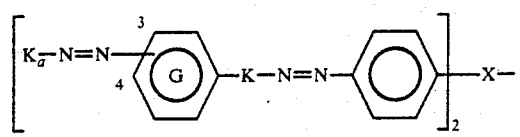

wherein $K_a$, K, X and G are defined in Table III below and anion $A^\ominus$ is $Cl^\ominus$ may be prepared by a method analogous to that of Example 1 from appropriate starting materials.

TABLE III

| EX. No. | K | Position of azo group on Ring G | $K_a$ | X |
|---|---|---|---|---|
| 182 | $K_2$ | 3 | [structure: pyridone with $NH_2$, $CH_3$, $(CH_2)_3N(CH_2)_3NHCO$—, $H_2N$—, $N-(CH_2)_3N(CH_3)_2$, =O] | $X_{34}'$ |
| 183 | $K_2$ | 4 | " | $X_{34}'$ |
| 184 | $K_3$ | 3 | " | $X_{34}'$ |
| 185 | $K_3$ | 4 | " | $X_{34}'$ |
| 186 | $K_1$ | 3 | " | $X_{34}'$ |
| 187 | $K_1$ | 4 | " | $X_{34}'$ |
| 188 | $K_2$ | 3 | " | $X_{11}$ |
| 189 | $K_3$ | 3 | " | $X_2'$ |
| 190 | $K_2$ | 3 | [structure: pyridine with $(CH_3)_2N(CH_2)_3HN$—, $CH_3$, CN, $NH(CH_2)_3N(CH_3)_2$] | $X_{34}'$ |
| 191 | $K_2$ | 4 | " | $X_{34}'$ |
| 192 | $K_3$ | 3 | " | $X_{34}'$ |
| 193 | $K_1$ | 3 | " | $X_{34}'$ |
| 194 | $K_2$ | 3 | [structure: naphthalene with $CH_3$, OH, $CONH(CH_2)_3N(CH_3)_2$] | $X_{34}'$ |
| 195 | $K_3$ | 3 | " | $X_{34}'$ |
| 196 | $K_1$ | 3 | " | $X_{34}'$ |
| 197 | $K_2$ | 3 | [structure: phenyl-N($C_2H_5$)($C_2H_4$—$\overset{\oplus}{N}(CH_3)_3$) $A^\ominus$] | $X_{34}'$ |
| 198 | $K_1$ | 3 | " | $X_{34}'$ |
| 199 | $K_2$ | 3 | [structure: phenyl-N($C_2H_5$)($C_2H_4$—pyridinium$^\oplus$) $A^\ominus$] | $X_{34}'$ |
| 200 | $K_1$ | 3 | " | $X_{34}'$ |

TABLE III-continued

| EX. No. | K | Position of azo group on Ring G | $K_a$ | X |
|---|---|---|---|---|
| 201 | $K_1$ | 3 | (structure: pyridone with HOCH₂CH₂NH-C(=O)-, NH₂, CH₃, N-CH₂CH₂OH, =O) | $X_{34'}$ |
| 202 | $K_1$ | 3 | (structure: pyridone with HOCH₂CH₂NH-C(=O)-, NH₂, NHCH₂CH₂OH, N-CH₂CH₂OH, =O) | $X_{34'}$ |

Dyeing Example A

70 Parts of chemically bleached sulphite cellulose (from pinewood) and 30 parts of chemically bleached sulphite cellulose (from birchwood) are ground in a Hollander in 2000 parts of water. 0.2 Parts of the dyestuff of in Example 1 are sprinkled into this pulp. After mixing for 20 minutes, paper is produced from this pulp. The absorbent paper obtained in this way is dyed yellow. The waste water is practically colourless.

Dyeing Example B 0.5 Parts of the dyestuff of Example 1 are dissolved in 100 parts of hot water and cooled to room temperature. This solution is added to 100 parts of chemically bleached sulphite cellulose which have been ground in a Hollander with 2000 parts of water. After thorough mixing for 15 minutes, sizing takes place. Paper so produced has a yellow shade of average intensity, with good wet fastness.

Dyeing Example C

An absorbent length of unsized paper is drawn through a dyestuff solution of the following composition at 40° to 50°: 0.5 Parts of the dyestuff of Example 1, 0.5 parts of starch and 99.0 parts of water. The excess dyestuff solution is squeezed out through two rollers. The dried length of paper is dyed yellow with good fastness.

Dyeing Example D

2 Parts of the dyestuff of Example 1 are dissolved at 40° in 4000 parts of softened water. 100 Parts premoistened cotton fabric are entered into the bath, which is heated for 30 minutes to boiling. The bath is kept at boiling for 1 hour, and the water which evaporates is replaced from time to time. The dyeing is then removed from the liquor, rinsed with water and dried. The dyestuff is absorbed practically quantitatively on the fibres; the dye bath is practically colourless. A yellow dyeing is obtained with good light fastness and good wet fastness.

Dyeing Example E

100 Parts of freshly tanned and neutralised chrome grain leather are milled for 30 minutes in a cask containing a bath of 250 parts of water at 55° and 1 part of the dyestuff of Example 1 (in acid addition salt form) and are treated for a further 30 minutes in the same bath with 2 parts of an anionic fat liquor based on sulphonated train oil. The leathers are dried and finished in the usual manner. An evenly dyed leather is obtained in yellow shades.

Further low-affinity, vegetable-tanned leathers may be dyed similarly in accordance with known methods.

Instead of using the compound of Example 1 in any one of Dyeing Examples A to E above, an appropriate amount of any one of the compounds of Example 2 to 202 may be used.

What is claimed is:

1. A metal-free compound or a 1:1 or 1:2 metal complex of the formula

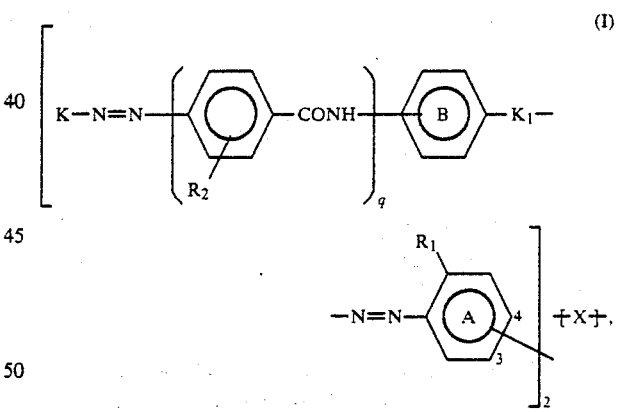

wherein each K is independently

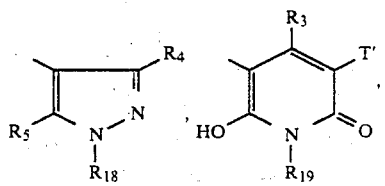

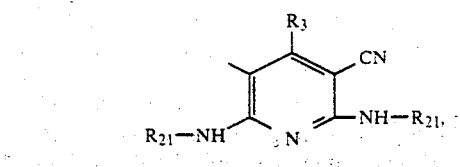

-continued

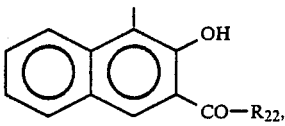

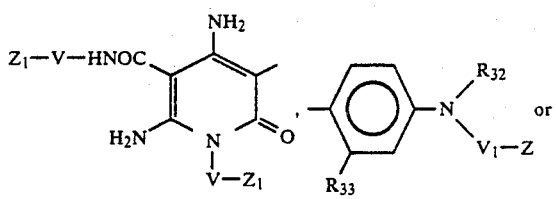

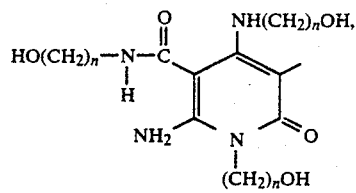

wherein
$R_3$ is hydrogen, $C_{1-4}$alkyl, phenyl or benzyl,
$R_4$ is $C_{1-4}$alkyl, $(C_{1-4}$alkoxy$)$-carbonyl or $-CO-N(R_8)_2$,
$R_5$ is amino or hydroxy,
$R_{18}$ is hydrogen, $C_{1-4}$alkyl,

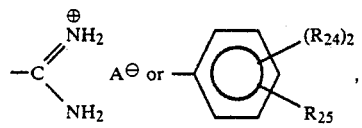

wherein
each $R_{24}$ is independently hydrogen, halo, $C_{1-4}$alkyl, $C_{1-4}$alkoxy, nitro, amino or acetamido, and
$R_{25}$ is hydrogen, $-NH-CO-(CH_2)_a-Z$, $-SO_2-NH-(CH_2)_d-Z$ or

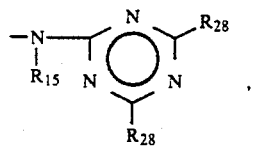

$R_{19}$ is hydrogen, $C_{1-6}$alkyl, amino, methylamino, phenylamino, $(C_{1-4}$alkoxy$)C_{1-4}$alkyl, phenyl-$(C_{1-4}$alkyl$)$, $-(CH_2)_d-CN$, $-(CH_2)_d-OH$, $-(CH_2)_m-Z$, $-(CH_2)_m-NR_{15}-CO-(CH_2)_a-Z$,

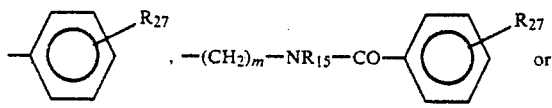

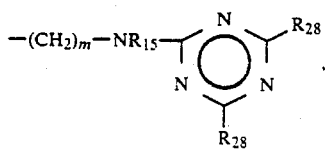

wherein $R_{27}$ is hydrogen, amino, methylamino, dimethylamino, diethylamino, acetamido, $-NH-CO-(CH_2)_a-Z$, $-(CH_2)_m-Z$, $-SO_2-NH-(CH_2)_m-Z$,

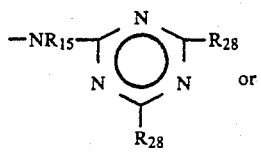

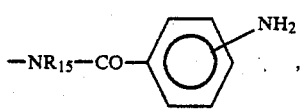

each $R_{21}$ is independently hydrogen, $C_{1-4}$alkyl, alkoxy$(C_{1-4}$alkyl$)$, 2-hydroxyethyl or $-(CH_2)_d-Z$,
$R_{22}$ is $-NH-(CH_2)_m-Z$ or nitrophenylamino,
$R_{32}$ is hydrogen, $-V_1-Z$, $C_{1-4}$alkyl or $C_{1-4}$hydroxyalkyl, wherein $V_1$ is linear $C_{1-4}$alkylene,
$R_{33}$ is hydrogen, $C_{1-4}$alkyl, $(C_{1-4}$alkyl$)$carbonylamino or $-NH-CO-V_1-Z$, wherein $V_1$ is linear $C_{1-4}$alkylene,
T' is hydrogen, cyano, carbamoyl or

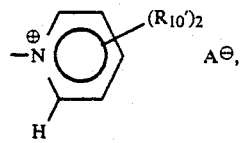

wherein each $R_{10}'$ is independently hydrogen, methyl, amino, dimethylamino or carbamoyl,
each V is independently linear $C_{1-12}$-alkylene; linear alkylene having a maximum of 12 carbon atoms interrupted by 1 or 2 members selected from the group consisting of $-S-$, $-O-$ and $-NR_8-$; $C_{3-12}$-alkenylene or alkenylene having a maximum of 12 carbon atoms interrupted by 1 or 2 members selected from the group consisting of $-S-$, $-O-$ and $-NR_8-$,
$V_1$ is linear $C_{1-4}$alkylene,
Z is $-N(R_{29})_2$ or $-N^{\oplus}(R_{30})_2R_{31}$ $A^{\ominus}$, wherein
each $R_{29}$ is independently hydrogen; $C_{1-4}$alkyl; phenyl$(C_{1-4}$-alkyl$)$ or $C_{2-4}$alkyl mono-substituted by hydroxy, halo or cyano or
$-N(R_{29})_2$ is morpholino, piperidino, pyrrolidino, piperazino or N-methylpiperazino,
each $R_{30}$ is independently $C_{1-4}$alkyl, phenyl$(C_{1-4}$-alkyl$)$ or $C_{2-4}$alkyl monosubstituted by hydroxy, halo or cyano, and
$R_{31}$ is $C_{1-4}$alkyl or phenyl$(C_{1-4}$-alkyl$)$ or
$-N^{\oplus}(R_{30})_2R_{31}$ $A^{\ominus}$ is pyridinium $A^{\ominus}$, picolinium $A^{\ominus}$, lutidinium $A^{\ominus}$,

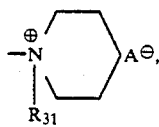

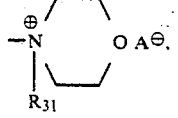

-continued

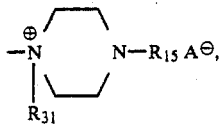

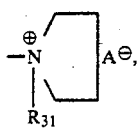

wherein R₃₁ is C₁₋₄-alkyl or phenyl(C₁₋₄-alkyl),
each Z₁ is independently —N(R₂₉)₂, —N⊕(R₃₀)₂R₃₁ A⊖ or hydroxy, wherein R₂₉, R₃₀ and R₃₁ are as defined above, and
each n is independently 1, 2, 3 or 4,
each K₁ is independently

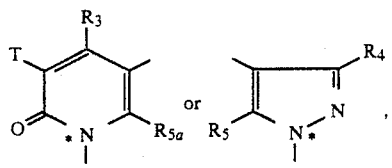

wherein
R₃ is hydrogen, C₁₋₄alkyl, phenyl or benzyl,
R₄ is C₁₋₄alkyl, (C₁₋₄alkoxy)-carbonyl or —CO—N(R₈)₂,
R₅ is amino or hydroxy,
R₅ₐ is hydroxy,
T is hydrogen, cyano,

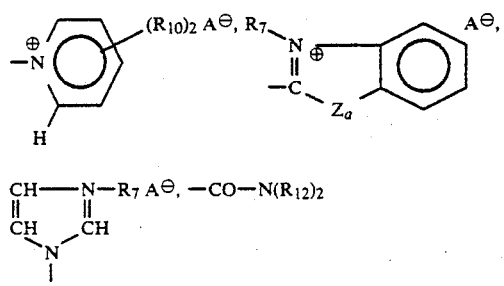

or (C₁₋₄alkyl)carbonyl, wherein
R₇ is C₁₋₄alkyl,
  each R₁₀ is independently hydrogen, C₁₋₄alkyl, —N(R₁₂)₂ or —CO—N(R₁₂)₂, wherein R₁₂ is as defined below,
  each R₁₂ is independently hydrogen, cyclohexyl, C₁₋₄alkyl or C₁₋₄hydroxyalkyl,
  Zₐ is —S—, —O— or —NR₈—, and
  the * denotes the atom attached to Ring B,
each R₁ is independently hydrogen, halo, hydroxy, C₁₋₄alkoxy or C₁₋₄alkyl, or
R₁ and R₅, located on rings attached to the same azo radical, are —O—Me—NH— or —O—Me—O—, wherein Me is a 1:1 or 1:2 metal complex-forming metal ion, or
R₁ and R₅ₐ, located on rings attached to the same azo radical, are —O—Me—O—, wherein Me is as defined above, each R₂ is independently hydrogen, halo, C₁₋₄alkyl or C₁₋₄alkoxy,
X is a direct bond, linear or branched C₁₋₄alkylene,

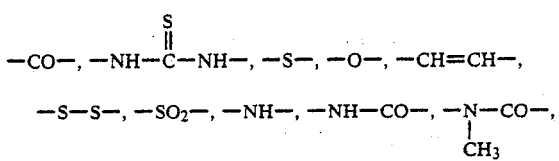

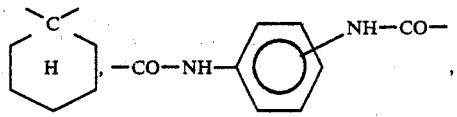

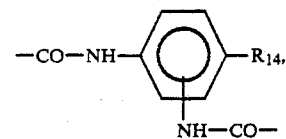

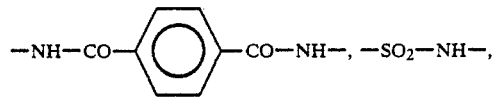

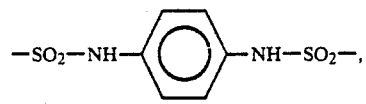

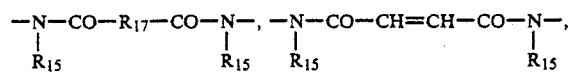

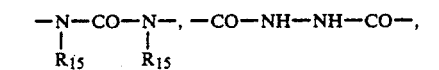

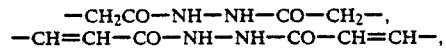

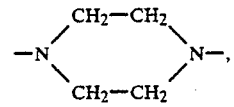

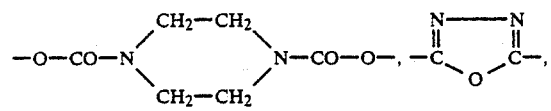

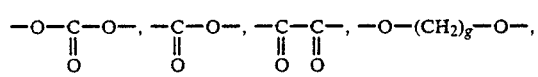

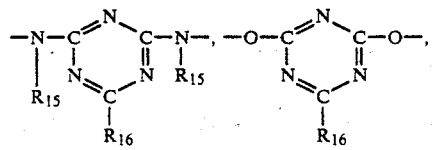

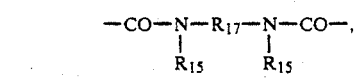

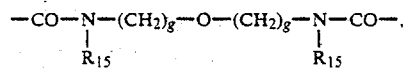

-continued

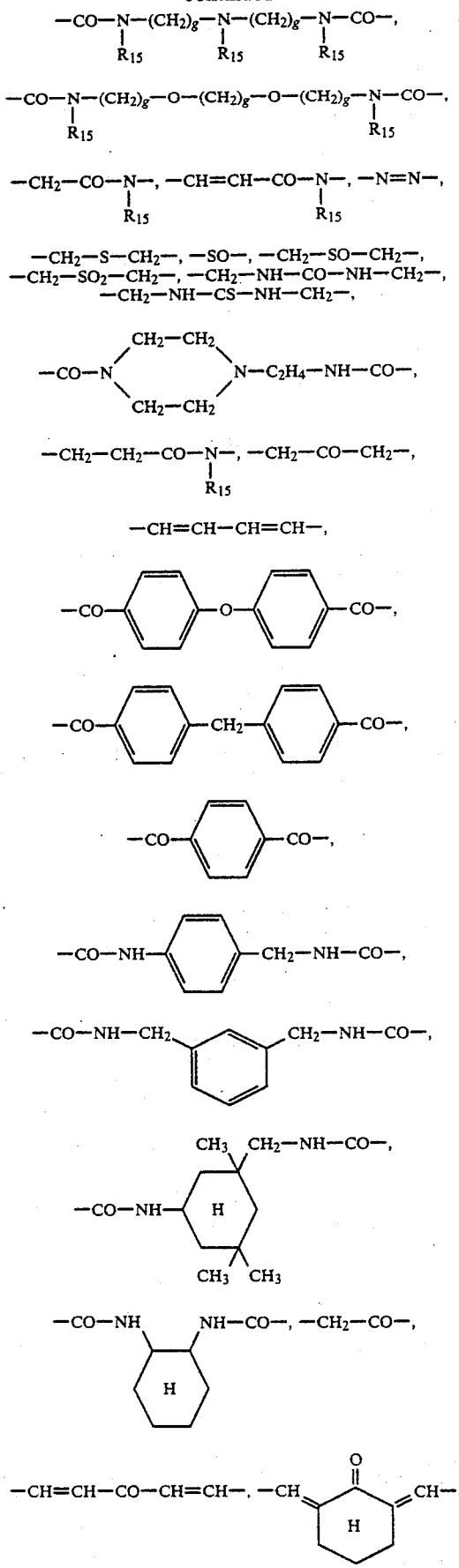

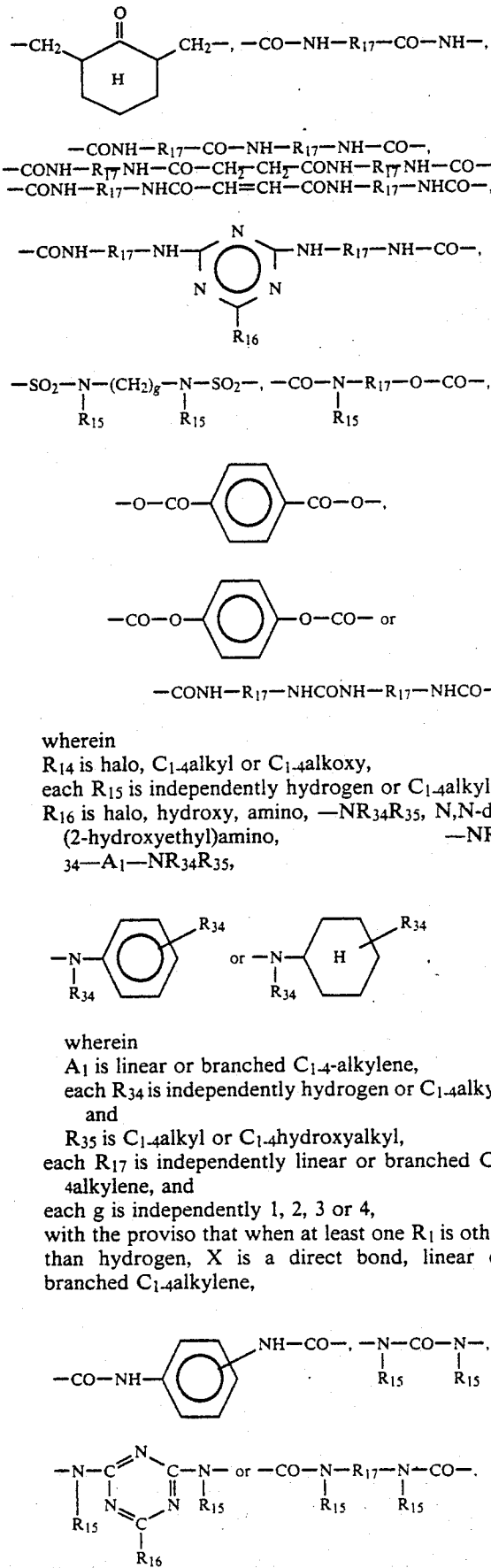

wherein
$R_{14}$ is halo, $C_{1-4}$alkyl or $C_{1-4}$alkoxy,
each $R_{15}$ is independently hydrogen or $C_{1-4}$alkyl,
$R_{16}$ is halo, hydroxy, amino, $-NR_{34}R_{35}$, N,N-di-(2-hydroxyethyl)amino, $-NR_{34}-A_1-NR_{34}R_{35}$, wherein
$A_1$ is linear or branched $C_{1-4}$-alkylene,
each $R_{34}$ is independently hydrogen or $C_{1-4}$alkyl, and
$R_{35}$ is $C_{1-4}$alkyl or $C_{1-4}$hydroxyalkyl,
each $R_{17}$ is independently linear or branched $C_{1-4}$alkylene, and
each g is independently 1, 2, 3 or 4,
with the proviso that when at least one $R_1$ is other than hydrogen, X is a direct bond, linear or branched $C_{1-4}$alkylene, wherein $R_{15}$–$R_{17}$ are as defined above, and each q is independently 0 or 1, wherein each $R_8$ is independently hydrogen or $C_{1-4}$alkyl,
each $R_{15}$ is independently hydrogen or $C_{1-4}$alkyl,
each $R_{28}$ is independently halo, hydroxy, amino, —NH—$C_2H_4OH$, —N($C_2H_4OH$)$_2$, —NH—(CH$_2$)$_m$—Z, —NH—(CH$_2$)$_d$—CN, —NH—(CH$_2$)$_d$—O—$C_{1-4}$alkyl, morpholino,

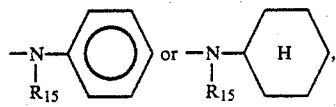

wherein
$R_{15}$ and Z are as defined above, and
d and m are as defined below,
each Z is independently as defined above,
each $A^{\ominus}$ is independently a non-chromophoric anion,
each a is independently 1 or 2,
each d is independently 2 or 3, and
each m is independently 1, 2, 3, 4, 5 or 6, with the provisos that (i) the compound of Formula I has at least two basic water-solubilizing groups, and (ii) each end of X is in the 3- or 4-position of the Ring A to which it is attached.

2. A metal-free compound or a 1:1 or 1:2 metal complex according to claim 1 wherein
each Me is independently iron, copper, cobalt, nickel, manganese or chromium in a 1:1 metal complex and cobalt, chromium, nickel or iron in a 1:2 metal complex.

3. A metal-free compound according to claim 2.
4. A 1:1 or 1:2 metal complex according to claim 2.
5. A metal-free compound or a 1:1 or 1:2 metal complex according to claim 2 wherein
each $R_{12}$ is independently hydrogen or $C_{1-4}$alkyl,
$R_{16}$ is chloro, hydroxy, amino, 2-hydroxyethylamino, di-(2-hydroxyethyl)amino, 3-diethylaminopropylamino, N-methyl-N-phenylamino or N-cyclohexyl-N-methylamino,
each $R_{17}$ is independently —(CH$_2$)$_d$—,
any ($C_{1-4}$alkoxy)$C_{1-4}$alkyl as $R_{19}$ or alkoxy-($C_{1-4}$alkyl) as $R_{21}$ is 3-methoxypropyl,
any m in $R_{22}$, $R_{27}$ or $R_{28}$ is 2 or 3,
$R_{32}$ is hydrogen, —(CH$_2$)$_d$—Z or $C_{1-4}$alkyl,
each V is independently —(CH$_2$)$_b$—, wherein b is 2, 3, 4, 5 or 6,
each $V_1$ is independently —(CH$_2$)$_d$—,
each g is independently 2, 3 or 4, and
each n is 2.

6. A metal-free compound or a 1:1 or 1:2 metal complex according to claim 1 having the formula

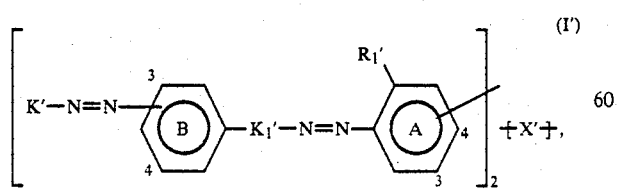

wherein
each K' is independently K, where K is as defined in claim 1,
each $K_1'$ is independently

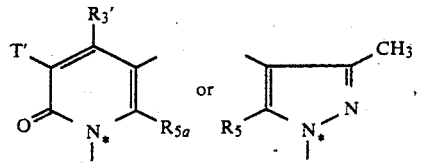

wherein
$R_3'$ is methyl, ethyl or phenyl,
$R_5$ is amino or hydroxy,
$R_{5a}$ is hydroxy,
T' is hydrogen, cyano, carbamoyl or

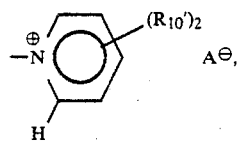

wherein each $R_{10}'$ is independently hydrogen, methyl, amino, dimethylamino or carbamoyl, and the * denotes the atom attached to Ring B,
each $R_1'$ is independently hydrogen, chloro, methyl, methoxy or hydroxy, or $A^{\ominus}$ is a non-chromophoric anion, $R_1'$ and $R_5$, located on rings attached to the same azo radical, are —O—Me—NH— or —O—Me—O—, wherein Me is a 1:1 or 1:2 metal complex-forming metal ion, or $R_1'$ and $R_{5a}$, located on rings attached to the same azo radical, are —O—Me—O—, wherein Me is as defined above, and X' is a direct bond, —CH$_2$—, —(CH$_2$)$_2$—, —(CH$_2$)$_3$—, —(CH$_2$)$_4$—, —S—, —O—, —CH=CH—, —NH—, —NHCO—, —N—CO—, —CO—NH—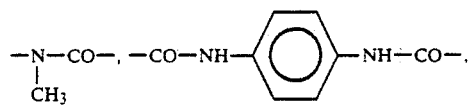NH—CO—,
|
CH$_3$ —CO—NH—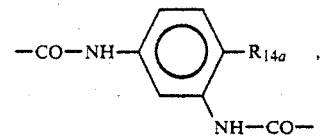—$R_{14a}$ ,
            |
            NH—CO—

—NH—CO—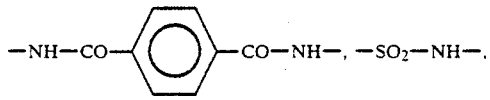—CO—NH—, —SO$_2$—NH—,

—NH—CO—CH$_2$—CH$_2$—CO—NH—,

—NH—CO—(CH$_2$)$_4$—CO—NH—,

—N—CO—(CH$_2$)$_2$—CO—N—,
|                              |
CH$_3$                          CH$_3$

—NH—CO—CH=CH—CO—NH—,

—N—CO—CH=CH—CO—N—, —NH—CO—NH—,
|                              |
CH$_3$                          CH$_3$

-continued $-\underset{\underset{CH_3}{|}}{N}-CO-\underset{\underset{CH_3}{|}}{N}-$, $-CO-NH-NH-CO-$,

[piperazine structure: $-N\langle\begin{smallmatrix}CH_2-CH_2\\CH_2-CH_2\end{smallmatrix}\rangle N-$]

[$-O-CO-N\langle\begin{smallmatrix}CH_2-CH_2\\CH_2-CH_2\end{smallmatrix}\rangle N-CO-O-$]

[oxadiazole structure], $-\underset{\underset{O}{\|}}{C}-\underset{\underset{O}{\|}}{C}-$, $-O-(CH_2)_g-O-$,

[triazine with N-CH$_3$ groups and $R_{16a}$], [triazine with NH groups and $R_{16a}$], $-CO-NH-(CH_2)_2-NH-CO-$, $-CO-NH-(CH_2)_3-NH-CO-$, $-CO-NH-(CH_2)_4-NH-CO-$, $-CO-\underset{\underset{CH_3}{|}}{N}-(CH_2)_2-\underset{\underset{CH_3}{|}}{N}-CO-$, $-CO-NH-CH_2-\underset{\underset{CH_3}{|}}{CH}-NH-CO-$, $-CO-NH-\underset{\underset{H_3C}{|}}{CH}-\underset{\underset{CH_3}{|}}{CH}-NH-CO-$, $-CH_2-CO-CH_2-$, $-CH=CH-CH=CH-$,

[$-CO-C_6H_4-O-C_6H_4-CO-$]

[$-CO-C_6H_4-CH_2-C_6H_4-CO-$]

[$-CO-C_6H_4-CO-$]

[$-CO-NH-C_6H_4-CH_2-NH-CO-$, $-CH_2-CO-$,]

$-CH=CH-CO-CH=CH-$, $-CO-NH-R_{17}-CO-NH-$, $-CONH-C_2H_4-CONH-C_2H_4NHCO-$, $-CONH-C_2H_4-NHCO-CH=CH-CONH-C_2H_4-NHCO-$.

-continued $-CONH-C_2H_4-NH-$[triazine with $R_{16a}$]$-NH-C_2H_4-NH-CO-$,

[$-CO-O-C_6H_4-O-CO-$] or $-CONH-C_2H_4-NHCONH-C_2H_4-NHCO-$, wherein $R_{14a}$ is hydrogen, chloro, methyl or methoxy, $R_{16a}$ is chloro, hydroxy, amino, 2-hydroxyethylamino, di-(2-hydroxyethyl)amino, 3-diethylaminopropylamino, N-methyl-N-phenylamino or N-cyclohexyl-N-methylamino, $R_{17}$ is linear or branched $C_{1-4}$alkylene, and g is 1, 2, 3 or 4, with the proviso that when at least one $R_1'$ is other than hydrogen, $X'$ is a direct bond, $-CH_2-$, $-(CH_2)_2-$, $-CO-NH-$[C$_6$H$_4$]$-NH-CO-$, $-NH-CO-NH-$, $-NH-$[triazine with $R_{16a}$]$-NH-$ or $-CO-NH-(CH_2)_2-NH-CO-$, wherein $R_{16a}$ is as defined above, with the provisos that (i) the compound of Formula I' has at least two basic water-solubilizing groups, (ii) each end of $X'$ is in the 3- or 4-position of the Ring A to which it is attached, and (iii) each azo radical attached to a Ring B is in the 3- or 4-position thereof.

7. A metal-free compound or a 1:1 or 1:2 metal complex according to claim 6 wherein $R_{17}$ is $-(CH_2)_d-$, any $(C_{1-4}$alkoxy$)C_{1-4}$alkyl as $R_{19}$ or (alkoxy)$C_{1-4}$-alkyl as $R_{21}$ is 3-methoxypropyl, $R_{32}$ is hydrogen, $-(CH_2)_d-Z$ or $C_{1-4}$alkyl, each V is independently $-(CH_2)_b-$, wherein b is 2, 3, 4, 5 or 6, each $V_1$ is independently $-(CH_2)_d-$, each Me is independently iron, copper, cobalt, nickel, manganese or chromium in a 1:1 metal complex and cobalt, chromium, nickel or iron in a 1:2 metal complex, independently g is independently 2, 3 or 4, any m in $R_{22}$, $R_{27}$ or $R_{28}$ is 2 or 3, and each n is 2.

8. A metal-free compound according to claim 7.

9. A 1:1 or 1:2 metal complex according to claim 7.

10. A metal-free compound or a 1:1 or 1:2 metal complex according to claim 6 having the formula

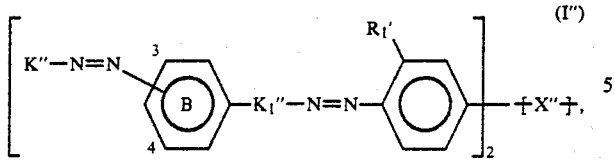
(I″)

wherein each K″ is independently

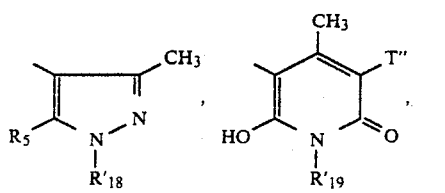,

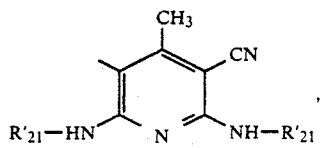,

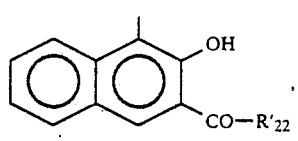,

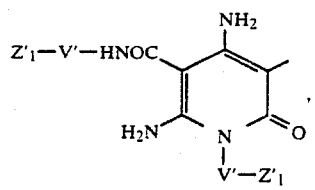,

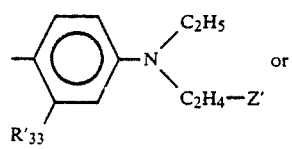

or

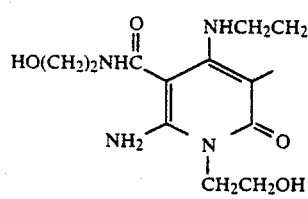,

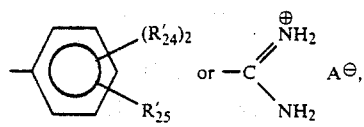

wherein
$R_5$ is amino or hydroxy,
$R_{18}'$ is hydrogen,

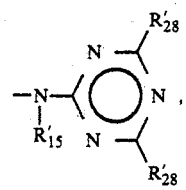, wherein
each $R_{24}'$ is independently hydrogen, chloro, methyl, methoxy or acetamido, and
$R_{25}'$ is hydrogen, —NH—CO—CH$_2$—Z', —SO$_2$—NH—(CH$_2$)$_d$—Z' or

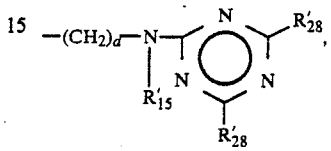, $R_{19}'$ is hydrogen, methyl, ethyl, benzyl, 2-phenylethyl, phenylamino, 2-cyanoethyl, 2hydroxyethyl, 3-methoxypropyl, —(CH$_2$)$_d$—Z',

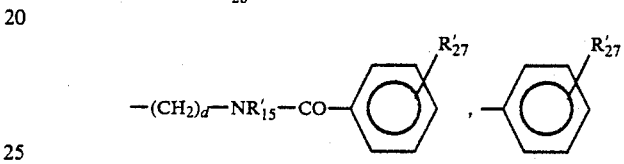

or —(CH$_2$)$_d$—NH—CO—CH$_2$—Z', wherein $R_{27}'$ is hydrogen, amino, dimethylamino, diethylamino, acetamido, —NH—CO—CH$_2$—Z', —(CH$_2$)$_d$—Z', —SO$_2$—NH—(CH$_2$)$_d$—Z' or

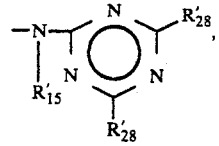

each $R_{21}'$ is independently hydrogen, methyl, ethyl, 2-hydroxyethyl, 3-methoxypropyl or —(CH$_2$)$_d$—Z',
$R_{22}'$ is —NH'(CH$_2$)$_d$—Z' or nitrophenylamino,
$R_{33}'$ is hydrogen, methyl, acetamido, propionamido or —NH—CO—(CH$_2$)$_d$—Z',
T″ is cyano or

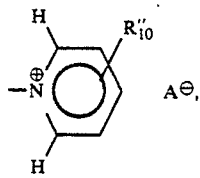, wherein $R_{10}''$ is hydrogen, methyl or amino,
each V' is independently —(CH$_2$)$_b$—, wherein b is 2, 3, 4, 5 or 6,
Z' is —N($R_{29}'$)$_2$ or —N$^⊕$($R_{30}'$)$_2$$R_{31}'$ A$^⊖$, wherein
each $R_{29}'$ is independently hydrogen, methyl or ethyl, or
—N($R_{29}'$) is morpholino, piperidino, piperazino or N-methylpiperazino,
each $R_{30}'$ is independently methyl or ethyl, and $R_{31}'$ is methyl, ethyl or benzyl, or
—N$^⊕$($R_{30}'$)$_2$$R_{31}'$ A$^⊖$ is pyridinium A$^⊖$, α-picolinium A$^⊖$ or β-picolinium A$^⊖$, and
each $Z_1'$ is independently —N($R_{29}'$)$_2$ or hydroxy, wherein $R_{29}'$ is as defined above, wherein each $R_{15}'$ is independently hydrogen or methyl,
each $R_{28}'$ is independently chloro, hydroxy, amino, phenylamino, cyclohexylamino, —NH—$C_2H_4OH$, —N($C_2H_4OH$)$_2$, 2-cyanoethylamino, 3-methoxypropylamino or —NH—(CH$_2$)$_d$—Z′, wherein Z′ is as defined above, and
d is as defined below,
each Z′ is independently as defined above, and
each d is independently 2 or 3,
each $K_1''$ is independently

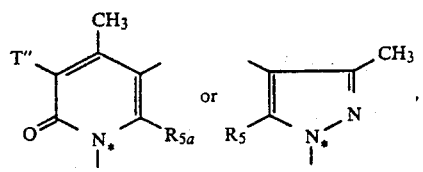

wherein
$R_5$ is amino or hydroxy,
$R_{5a}$ is hydroxy,
T″ is as defined above, and
the * denotes the atom attached to Ring B,
each $R_1'$ is independently hydrogen, chloro, methyl, methoxy or hydroxy, or
$R_1'$ and $R_5$, located on rings attached to the same azo radical, are —O—Me$_1$—NH— or —O—Me$_1$—O—, wherein Me$_1$ is copper in a 1:1 metal complex and cobalt, chromium or iron in a 1:2 metal complex, or
$R_1'$ and $R_{5a}$, located on rings attached to the same azo radical, are —O—Me$_1$—O—, wherein Me$_1$ is as defined above, and
X″ is a direct bond, —CH$_2$—, —(CH$_2$)$_2$—, —NH—CO—,

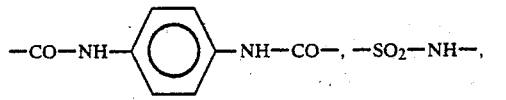

—NH—CO—CH$_2$—CH$_2$—CO—NH—,
—NH—CO—(CH$_2$)$_4$—CO—NH—,

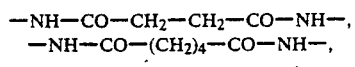

—NH—CO—CH=CH—CO—NH—,

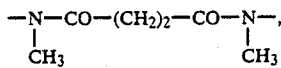

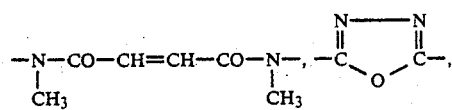

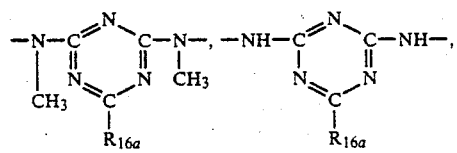

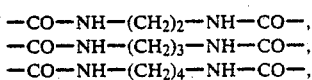

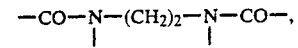

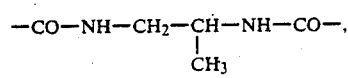

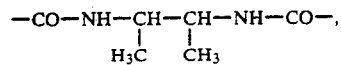

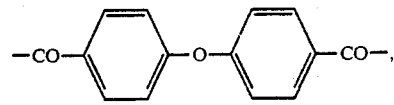

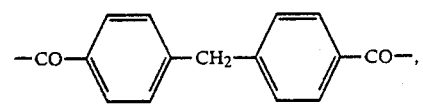

—CO—NH—$R_{17}$—CO—NH—,

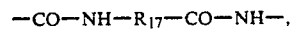

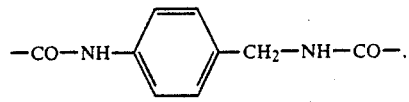

—CONH—C$_2$H$_4$—NHCO—CH=CH—CONH—C$_2$H$_4$—NHCO—,

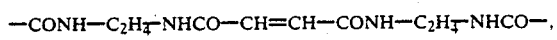 or

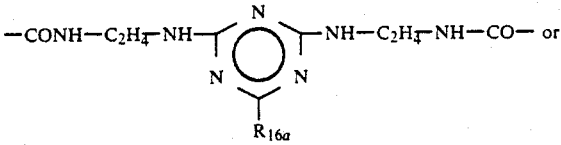

wherein
$R_{16a}$ is chloro, hydroxy, amino, 2-hydroxyethylamino, di-(2-hydroxyethyl)amino, 3-diethylaminopropylamino, N-methyl-N-phenylamino or N-cyclohexyl-N-methylamino, and
$R_{17}$ is linear or branched $C_{1-4}$alkylene,
with the proviso that when at least one $R_1'$ is other than hydrogen, X″ is a direct bond,
wherein each A$^\ominus$ is independently a non-chromophoric anion, with the provisos that (i) the compound of Formula I″ has at least two basic water-solubilizing groups, and (ii) each azo radical attached to a Ring B in the 3- or 4-position thereof.

11. A metal-free compound according to claim 10.

12. A metal-free compound according to claim 11 wherein
the two K′″s are identical,
the two $K_1'''$s are identical,
the two $R_1'''$s are identical, and
each azo radical attached to a Ring B is in the 3-position thereof or each azo radical attached to a Ring B is in the 4-position thereof.

13. A metal-free compound according to claim 10 having the formula

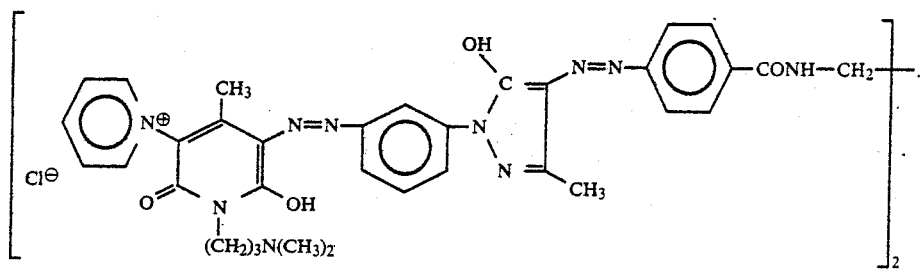
14. A 1:1 or 1:2 metal complex according to claim 10.
15. A 1:1 or 1:2 metal complex according to claim 14 wherein
the two K'''s are identical,
the two $K_1'''$s are identical,
the two $R_1''$s are identical, and
each azo radical attached to a Ring B is in the 3-position thereof or each azo radical attached to a Ring B is in the 4-position thereof.
* * * * *